United States Patent
Pedersen et al.

(10) Patent No.: US 12,138,449 B2
(45) Date of Patent: *Nov. 12, 2024

(54) TEMPORARY PACING LEAD

(71) Applicant: Nextern Innovation, LLC, White Bear Lake, MN (US)

(72) Inventors: Wesley Robert Pedersen, Minneapolis, MN (US); Paul Sorajja, Minneapolis, MN (US)

(73) Assignee: Nextern Innovation, LLC, White Bear Lake, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/295,542

(22) Filed: Apr. 4, 2023

(65) Prior Publication Data
US 2024/0058603 A1 Feb. 22, 2024

Related U.S. Application Data

(63) Continuation of application No. 17/004,520, filed on Aug. 27, 2020, now Pat. No. 11,642,518, which is a continuation of application No. 15/642,084, filed on Jul. 5, 2017, now Pat. No. 10,773,076.

(60) Provisional application No. 62/602,397, filed on Apr. 21, 2017, provisional application No. 62/495,765, filed on Sep. 23, 2016, provisional application No. 62/493,490, filed on Jul. 5, 2016.

(51) Int. Cl.
*A61N 1/05* (2006.01)

(52) U.S. Cl.
CPC ...... *A61N 1/056* (2013.01); *A61N 2001/0578* (2013.01)

(58) Field of Classification Search
CPC ............ A61N 1/056; A61N 2001/0578; A61N 1/0563; A61N 1/0595; A61N 1/0587; A61N 1/059; A61N 1/0592
See application file for complete search history.

(56) References Cited

U.S. PATENT DOCUMENTS

| | | |
|---|---|---|
| 4,325,374 A | 4/1982 | Komiya |
| 4,602,645 A | 7/1986 | Barrington et al. |
| 5,807,339 A | 9/1998 | Bostrom et al. |
| 5,851,226 A | 12/1998 | Skubitz et al. |
| 5,964,793 A | 10/1999 | Rutten et al. |
| 6,219,581 B1 | 4/2001 | Schaldach et al. |
| 6,324,435 B1 | 11/2001 | Shchervinsky et al. |
| 6,463,323 B1 | 10/2002 | Conrad-Vlasak et al. |
| 6,944,506 B1 | 9/2005 | Morgan et al. |
| 7,231,249 B2 | 6/2007 | Mower |
| 8,406,902 B2 | 3/2013 | Morgan et al. |

(Continued)

*Primary Examiner* — Jon Eric C Morales
(74) *Attorney, Agent, or Firm* — Thompson Patent Law Offices PC

(57) ABSTRACT

A temporary pacing lead has an atraumatic curled distal region with multiple cathodes and distal pressure measurement to allow positioning and repositioning within the heart chamber without fluoroscopic or echo guidance. The curled distal region provides definite contact with two opposing walls of the ventricular chamber to ensure electrical signal capture without trauma to the endocardial surface. A stylet located in the pacing lead lumen assists in introducing, placing, and removing the pacing lead from the heart. The flexible distal region provides safe removal of the temporary lead following completion of use.

20 Claims, 29 Drawing Sheets

(56) References Cited

U.S. PATENT DOCUMENTS

| | | |
|---|---|---|
| 8,731,659 B2 | 5/2014 | Hansen et al. |
| 8,825,157 B2 | 9/2014 | Warren et al. |
| 9,044,595 B2 | 6/2015 | Araya et al. |
| 9,216,280 B1 | 12/2015 | Hakki et al. |
| 9,289,593 B1 | 3/2016 | Hakki et al. |
| 9,387,323 B2 | 7/2016 | Fleischhacker et al. |
| 9,498,641 B2 | 11/2016 | Ward |
| 9,629,996 B2 | 4/2017 | Kast et al. |
| 10,773,076 B2 | 9/2020 | Pedersen et al. |
| 11,642,518 B1 * | 5/2023 | Pedersen ............... A61N 1/056 607/125 |
| 2002/0193836 A1 | 12/2002 | Schmidt |
| 2003/0014049 A1 | 1/2003 | Koblish et al. |
| 2003/0040676 A1 | 2/2003 | Prentice et al. |
| 2003/0199959 A1 | 10/2003 | Zhang et al. |
| 2006/0136001 A1 | 6/2006 | Ortega et al. |
| 2006/0167535 A1 | 7/2006 | Johnson |
| 2008/0097566 A1 | 4/2008 | Colliou |

* cited by examiner

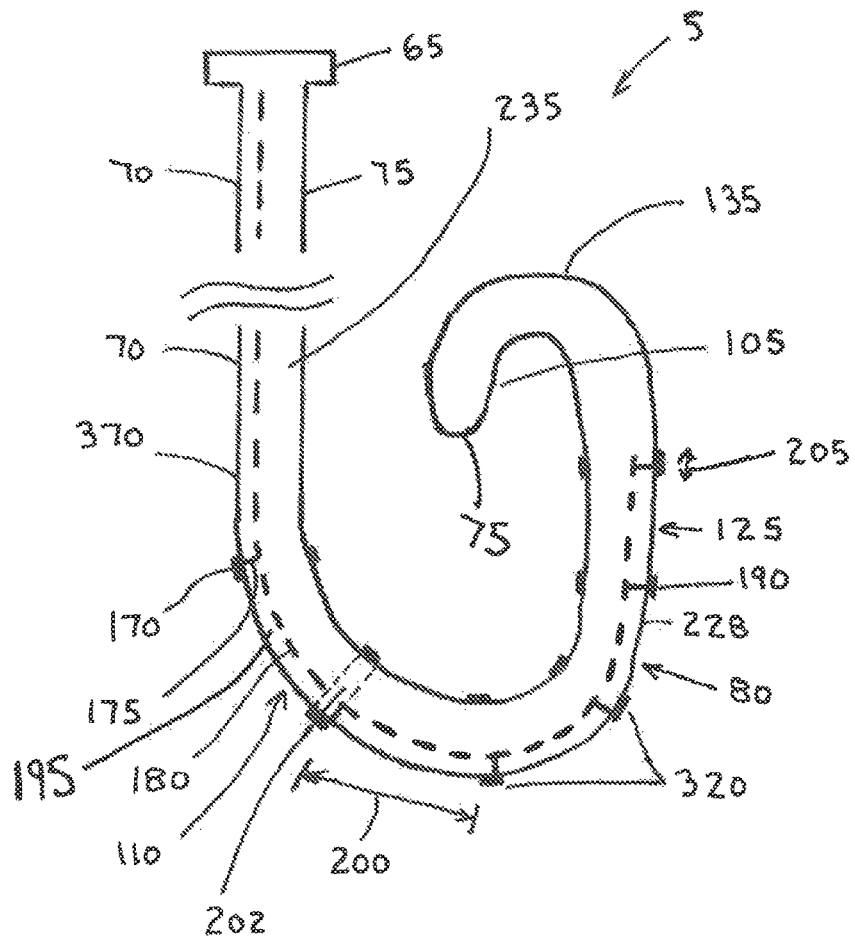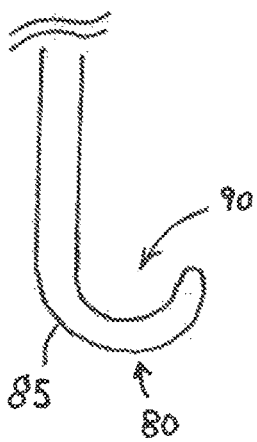

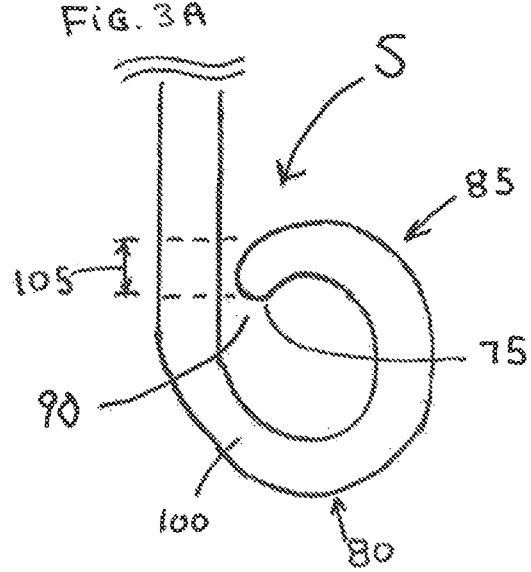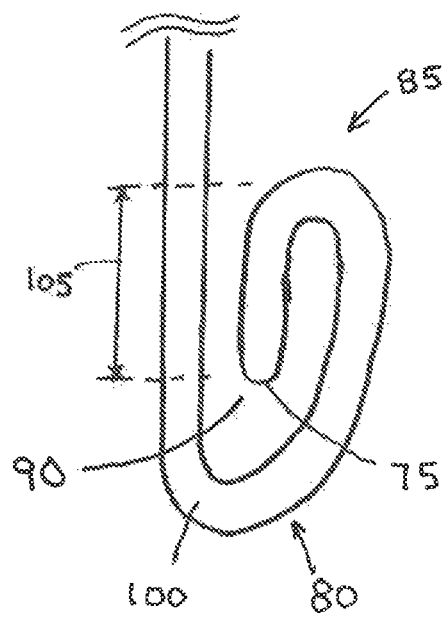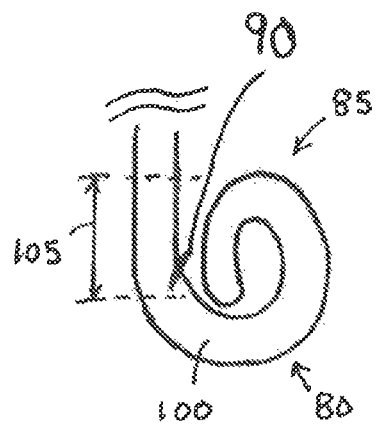

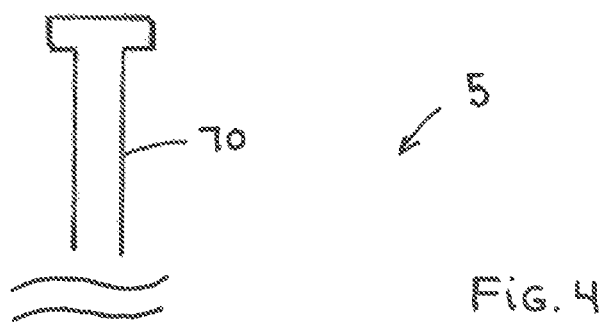
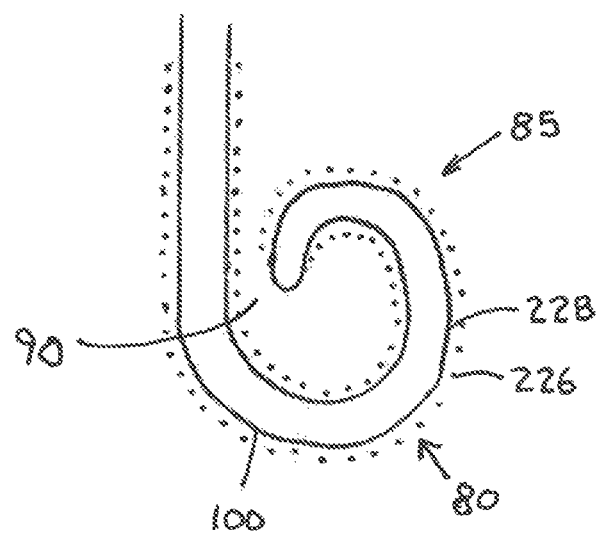
FIG. 4

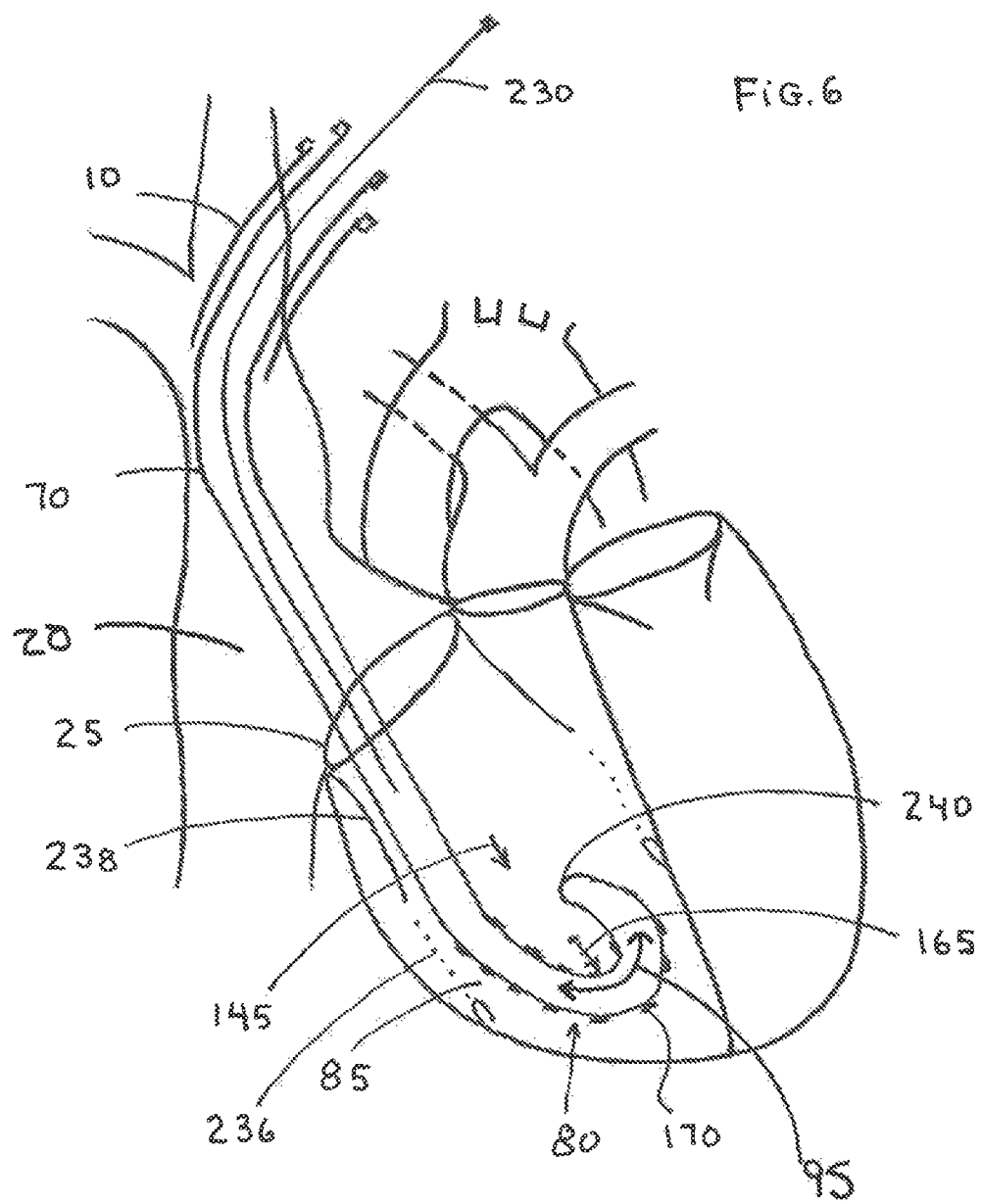

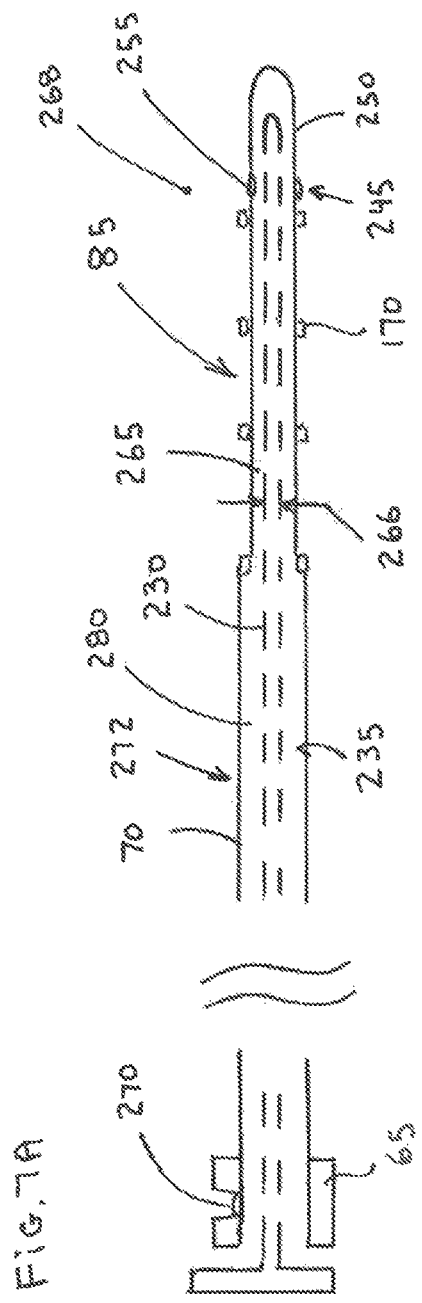
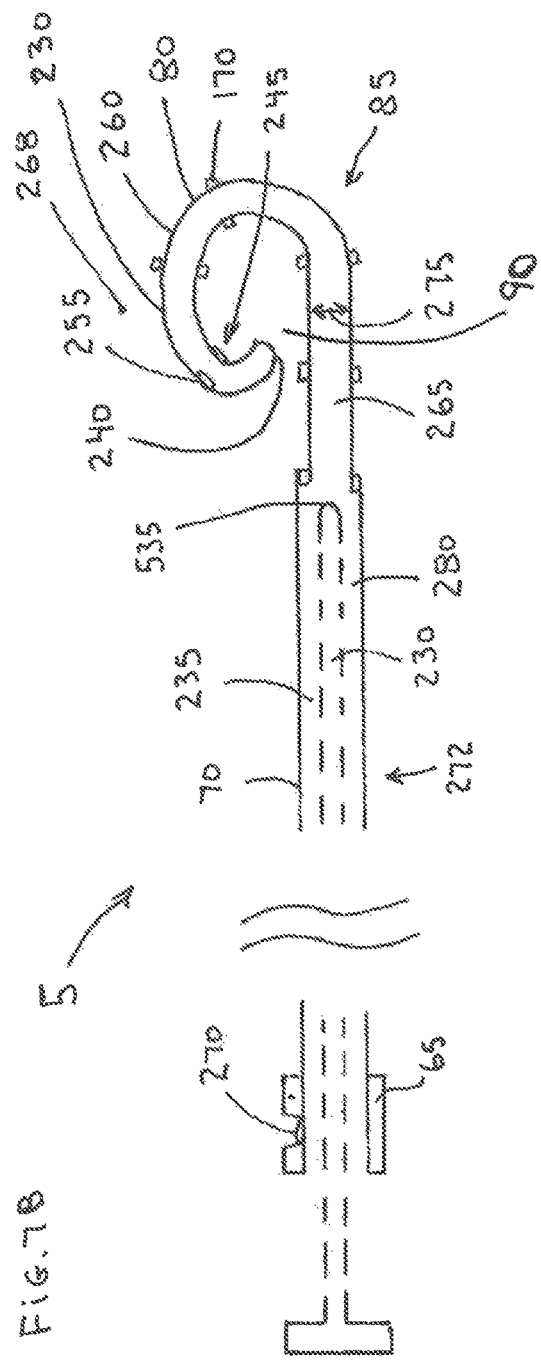

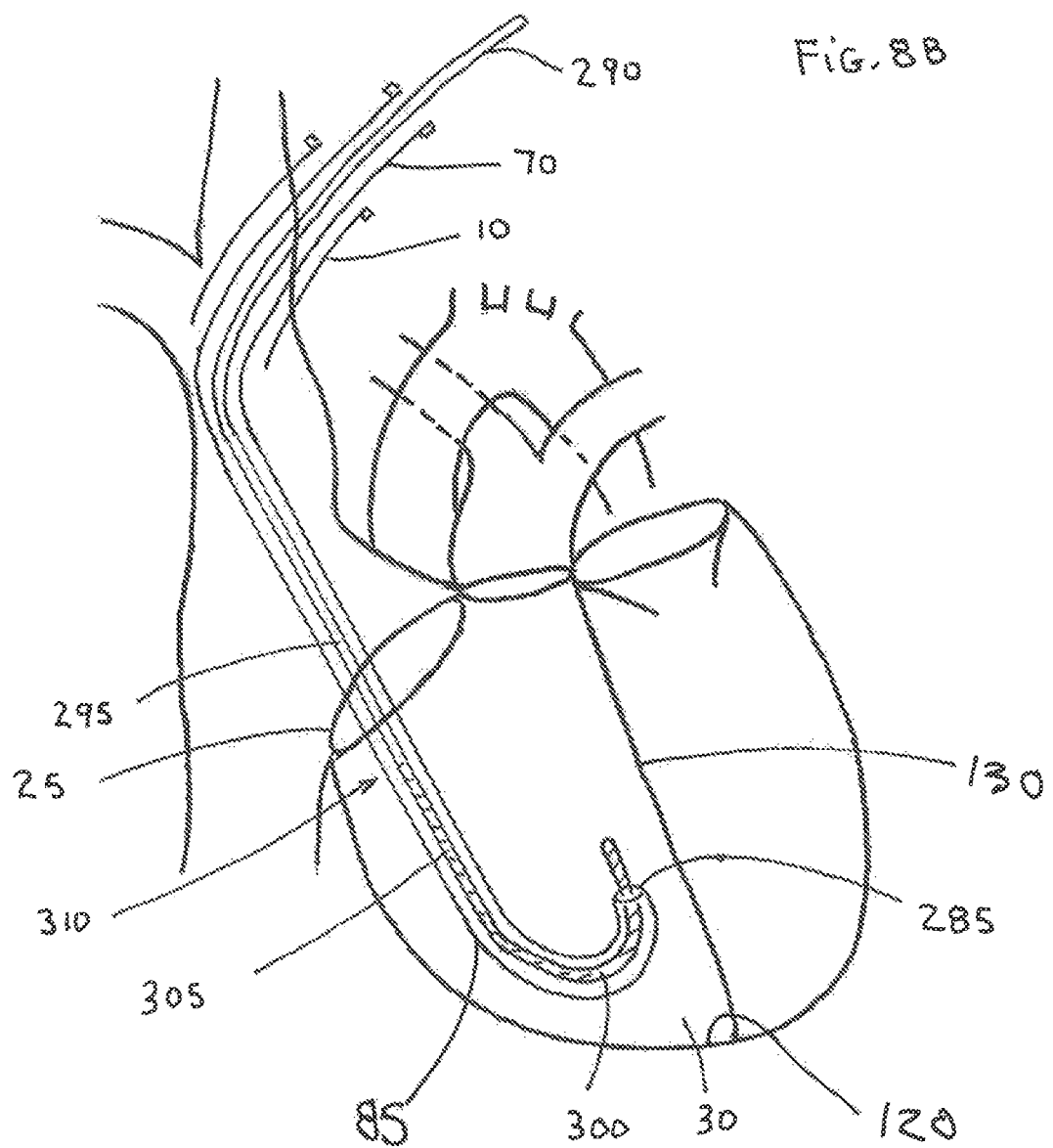

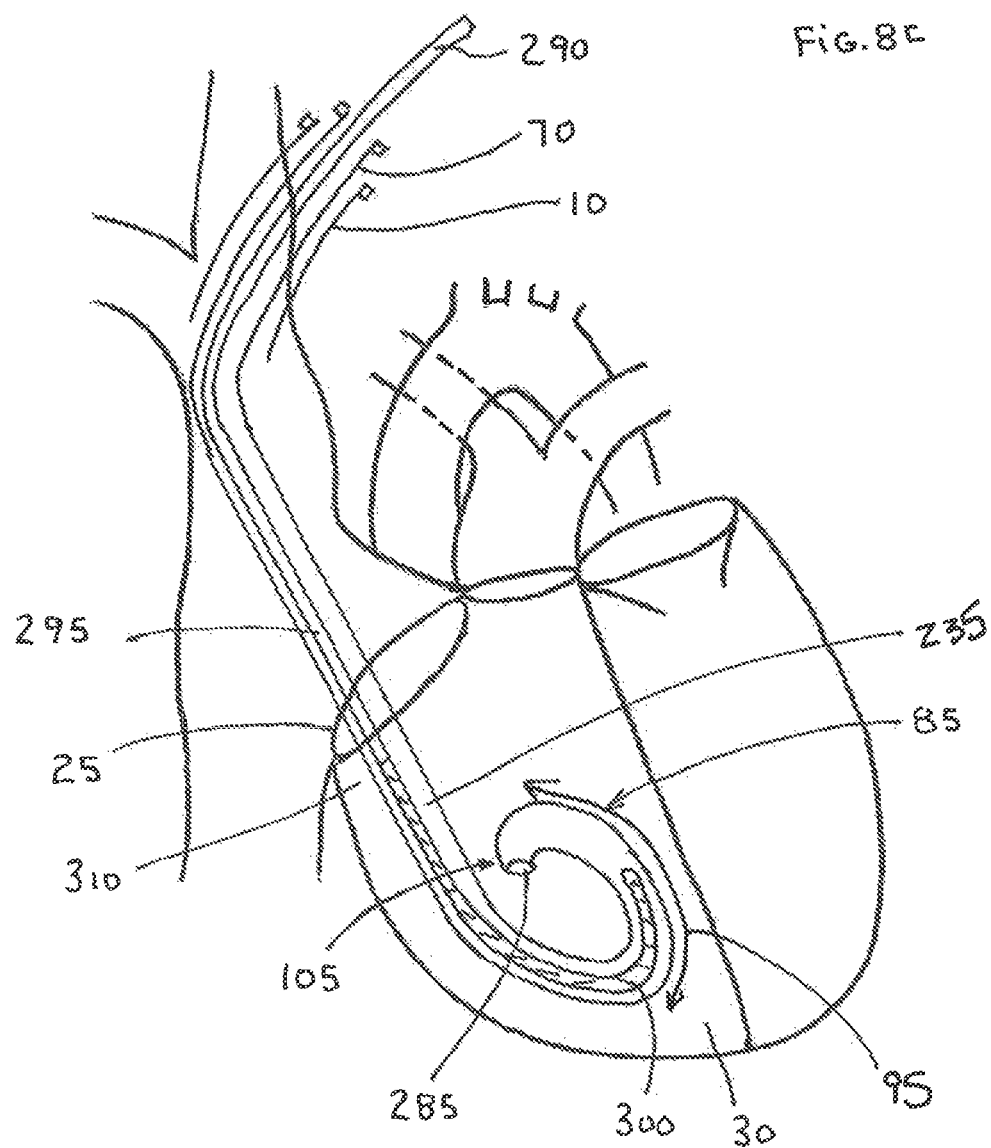

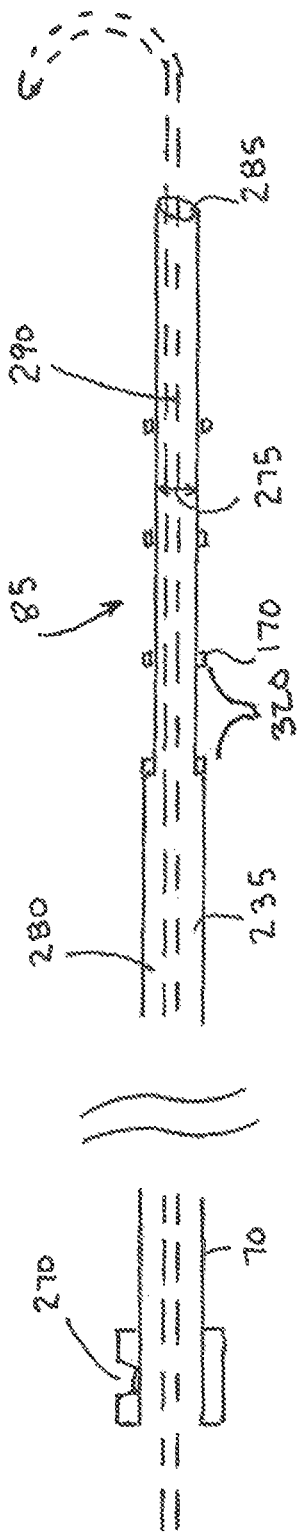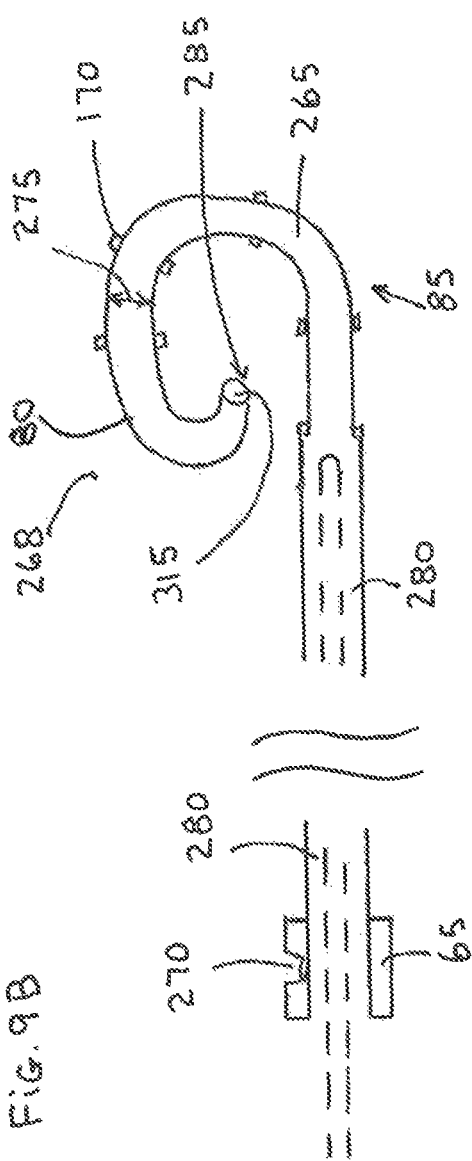

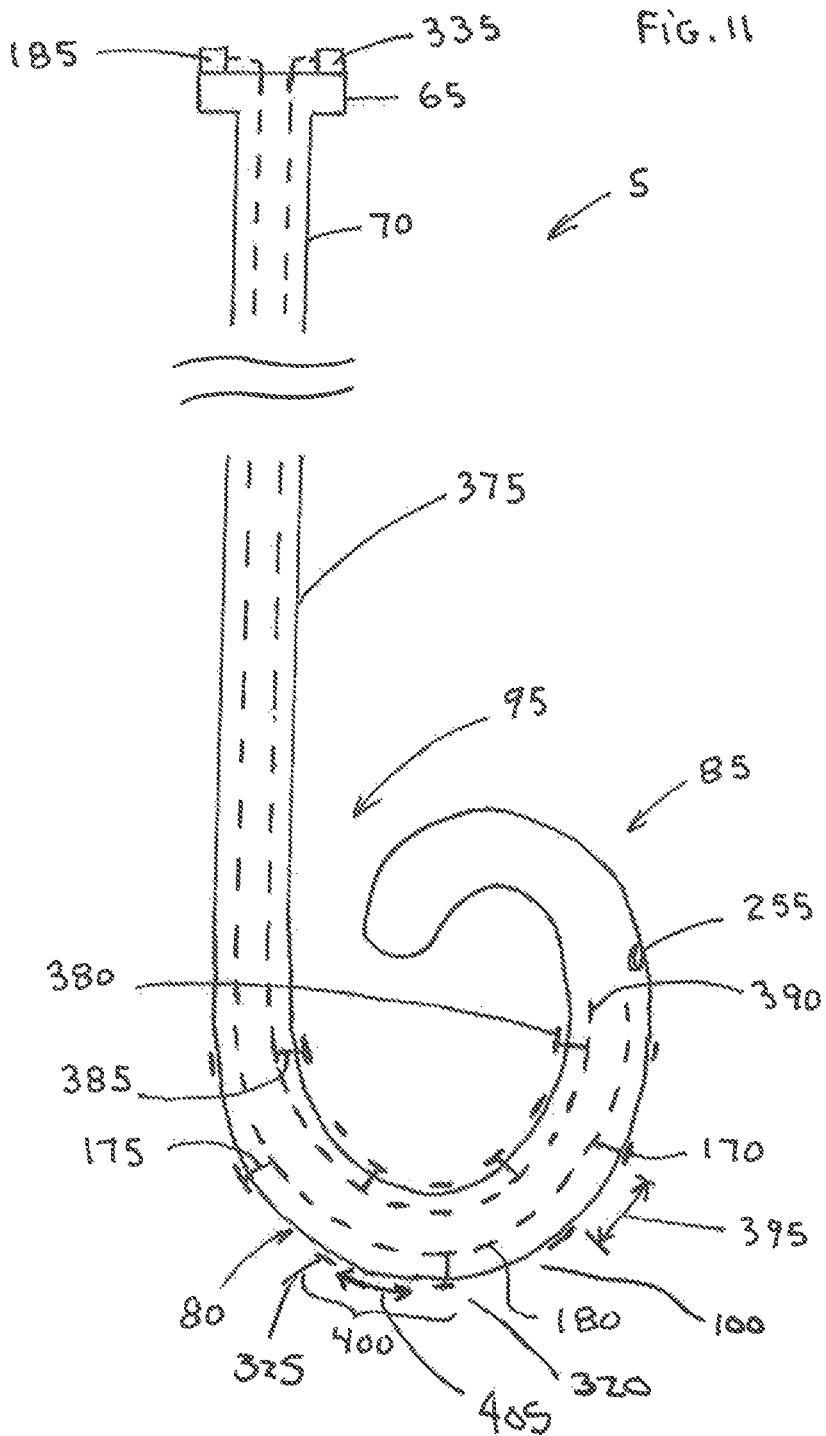

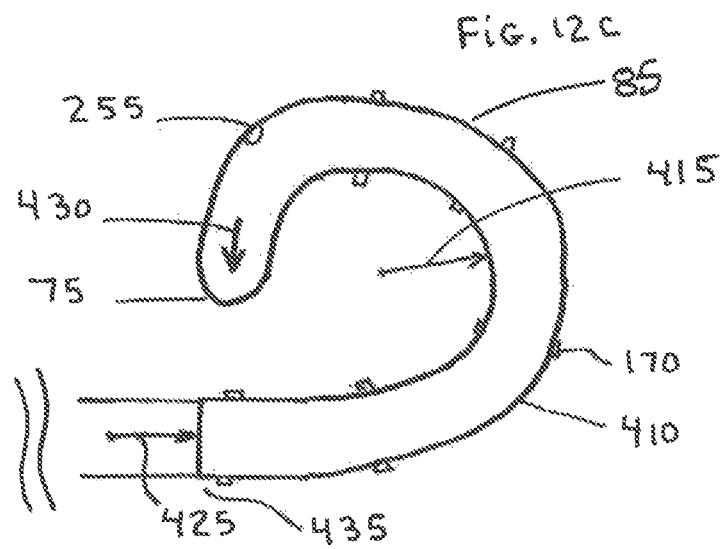
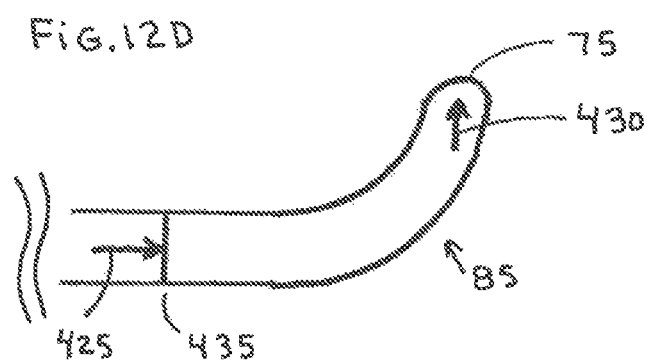
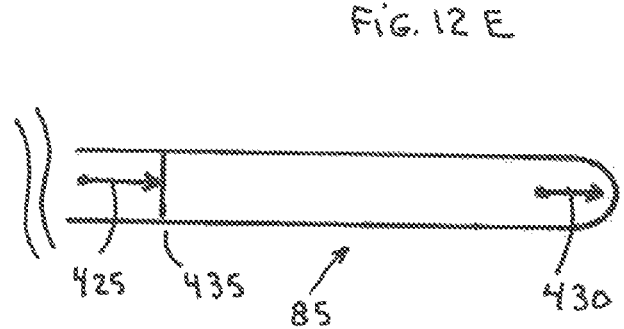

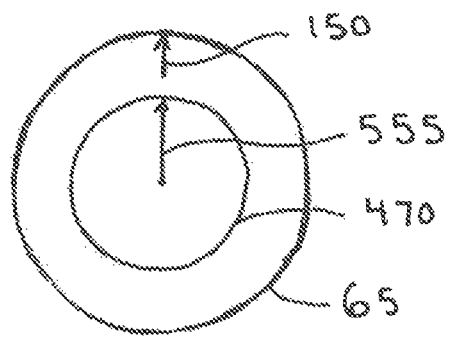

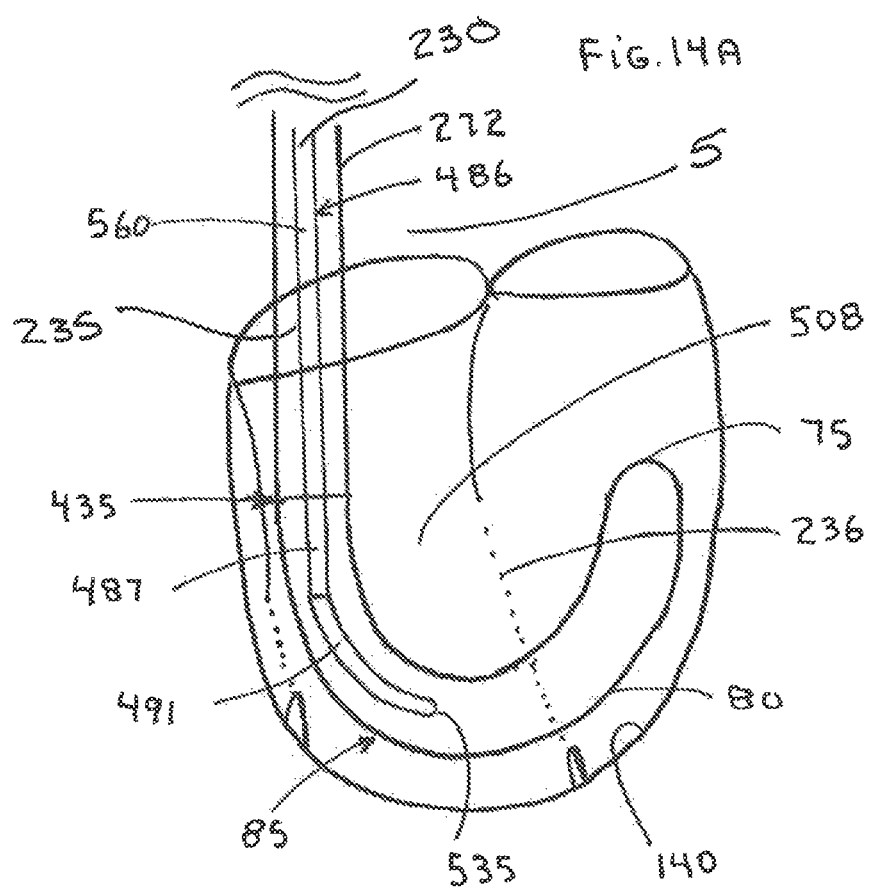
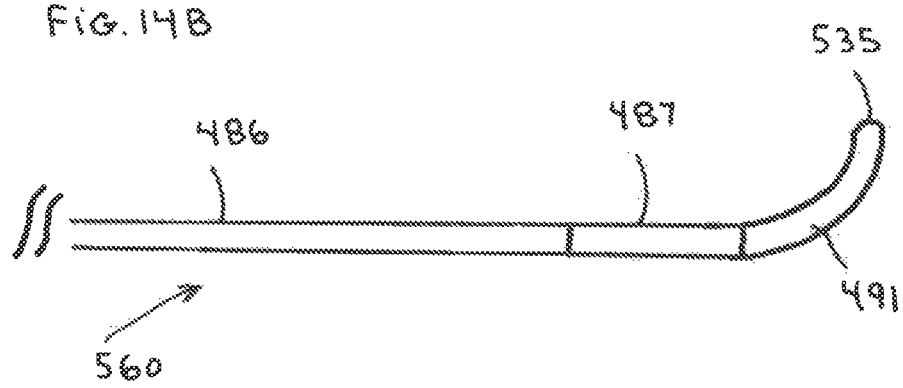

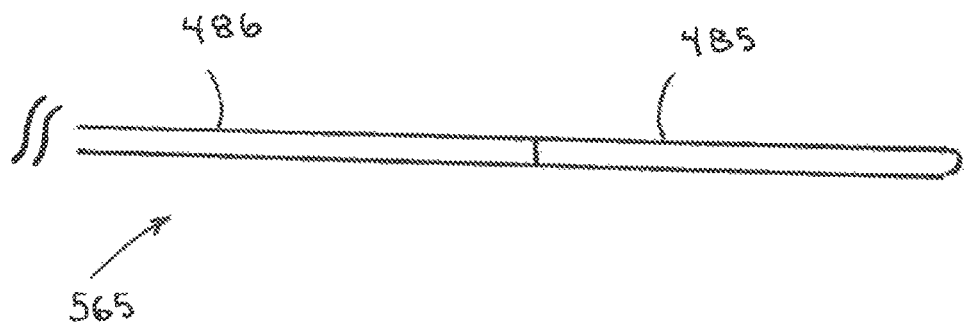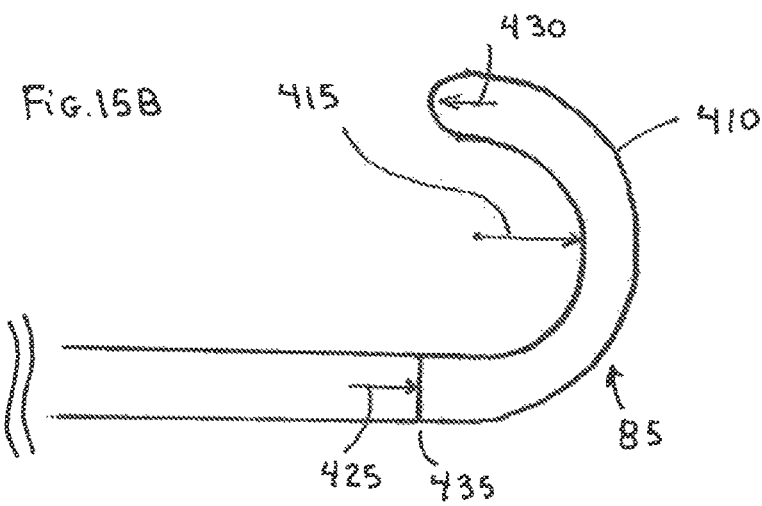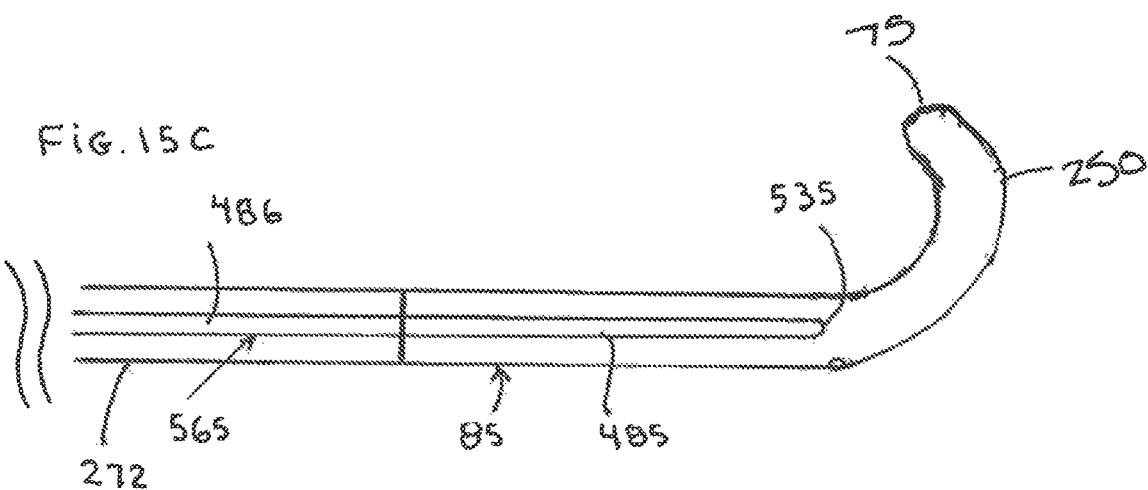

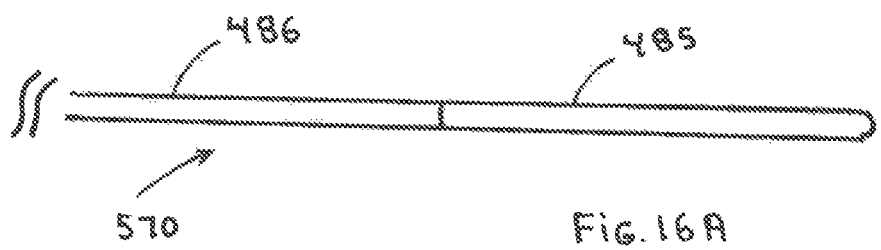
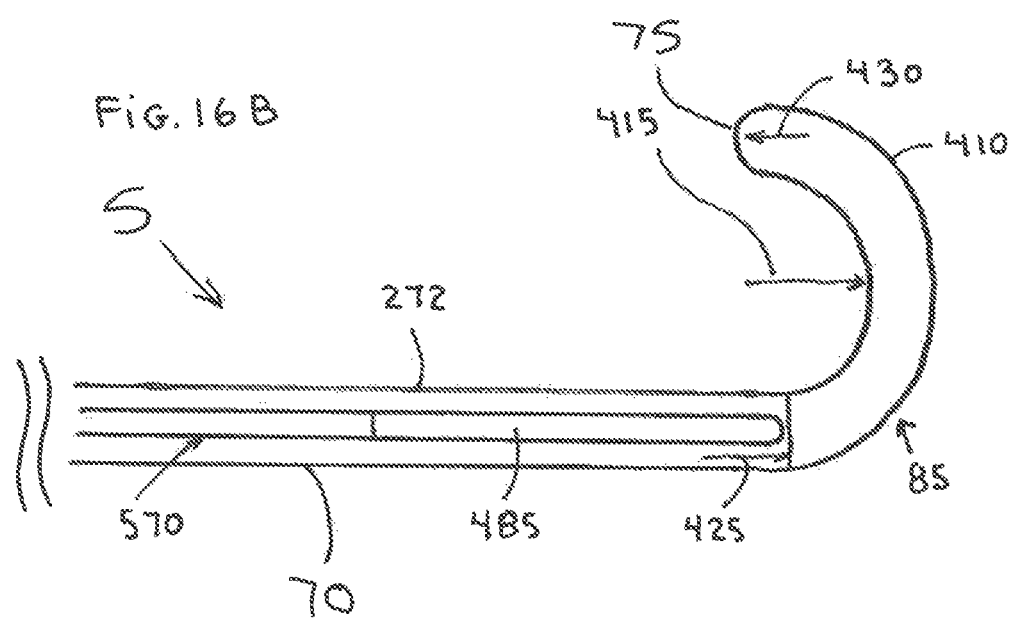

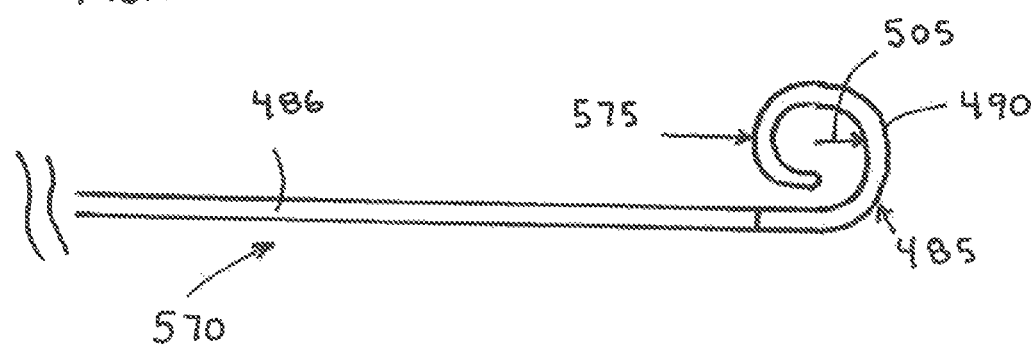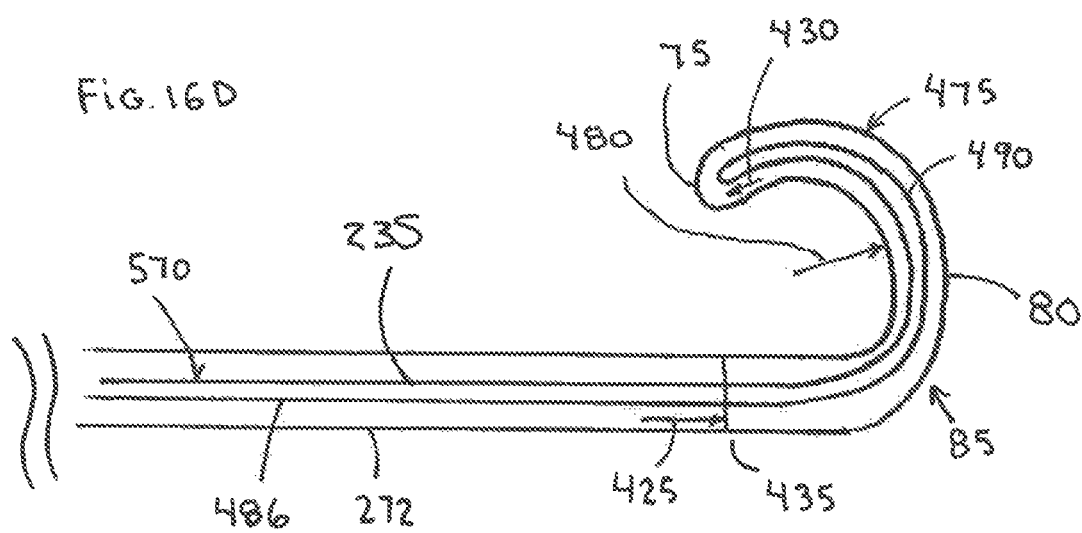

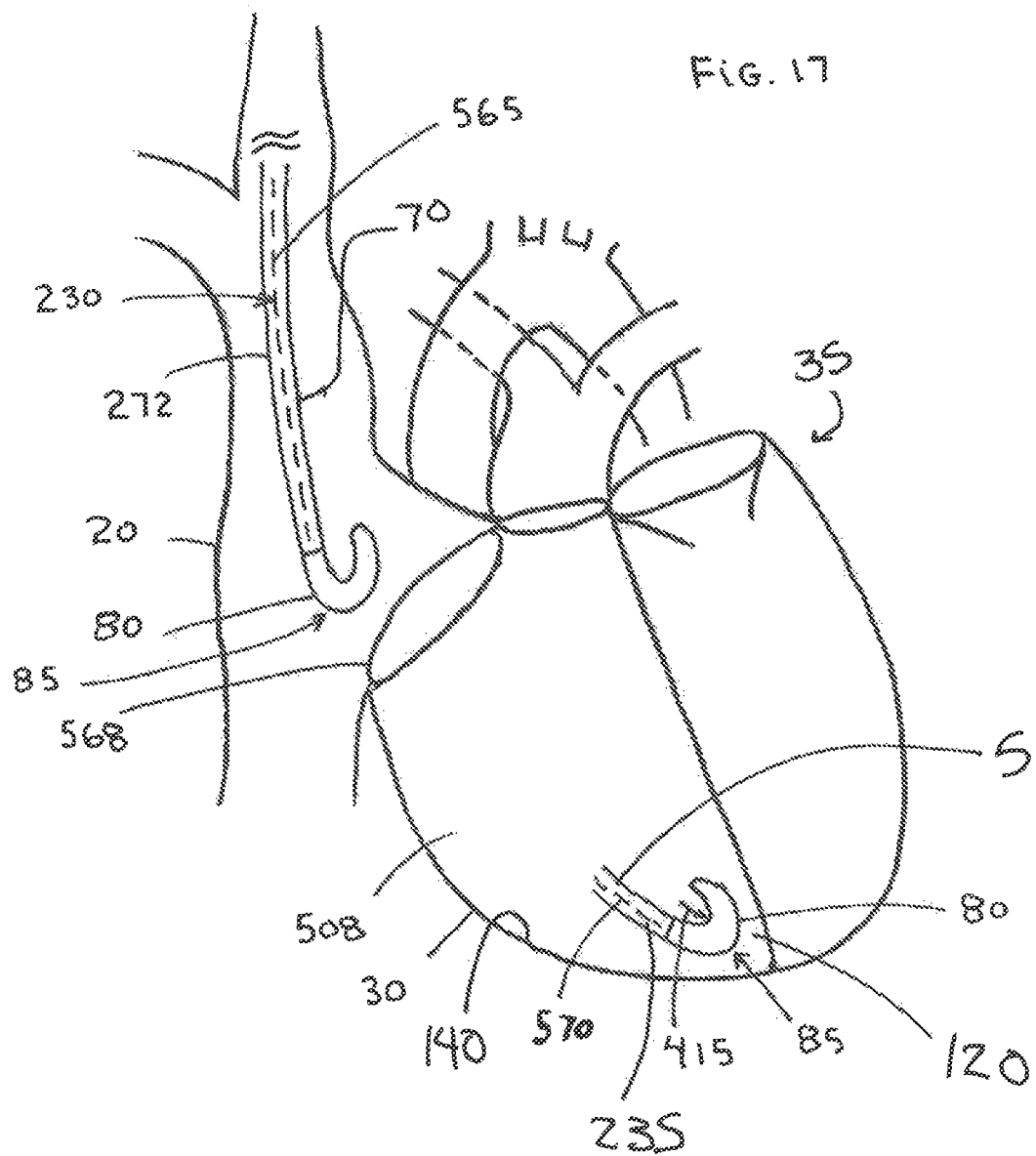

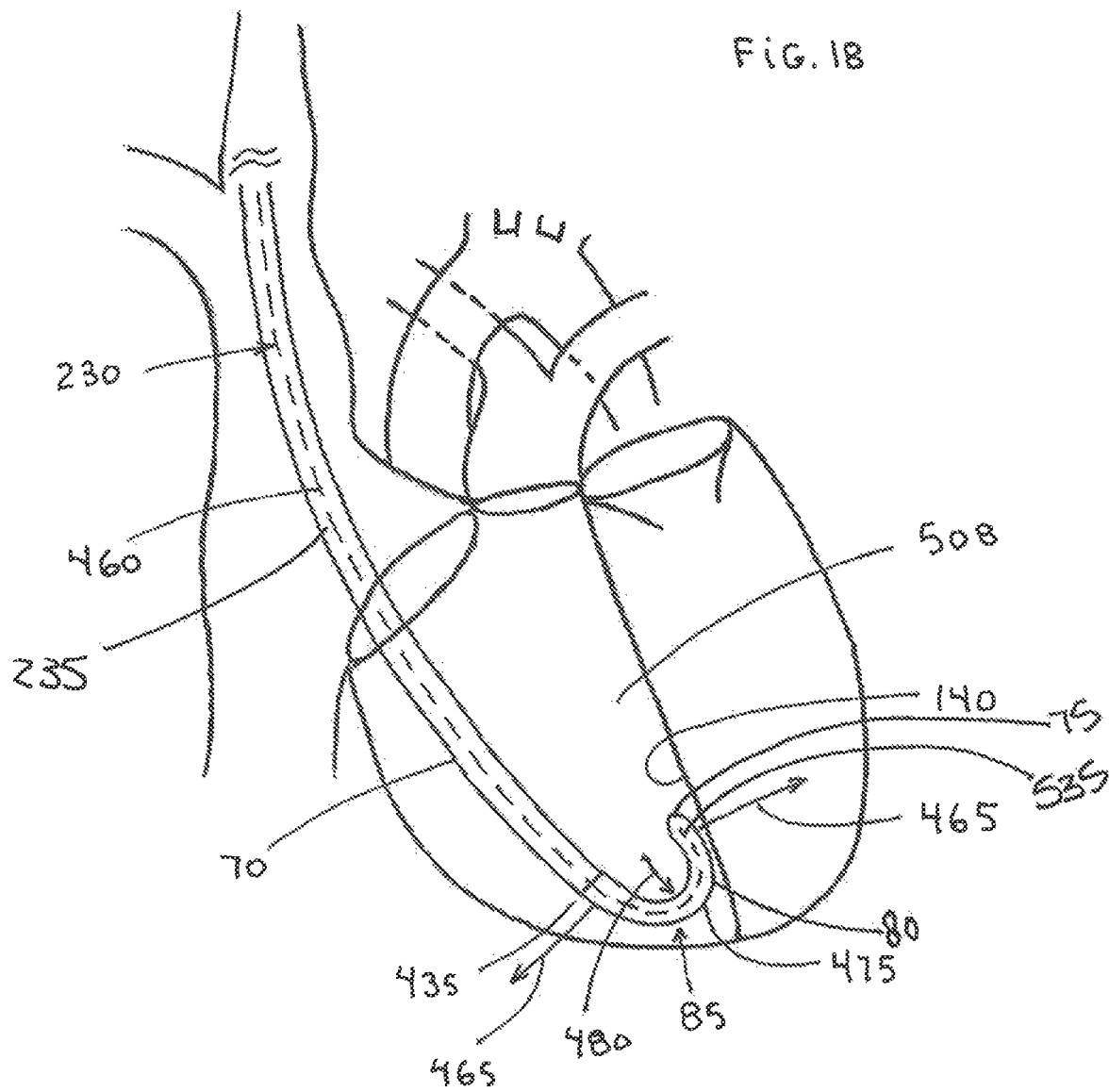

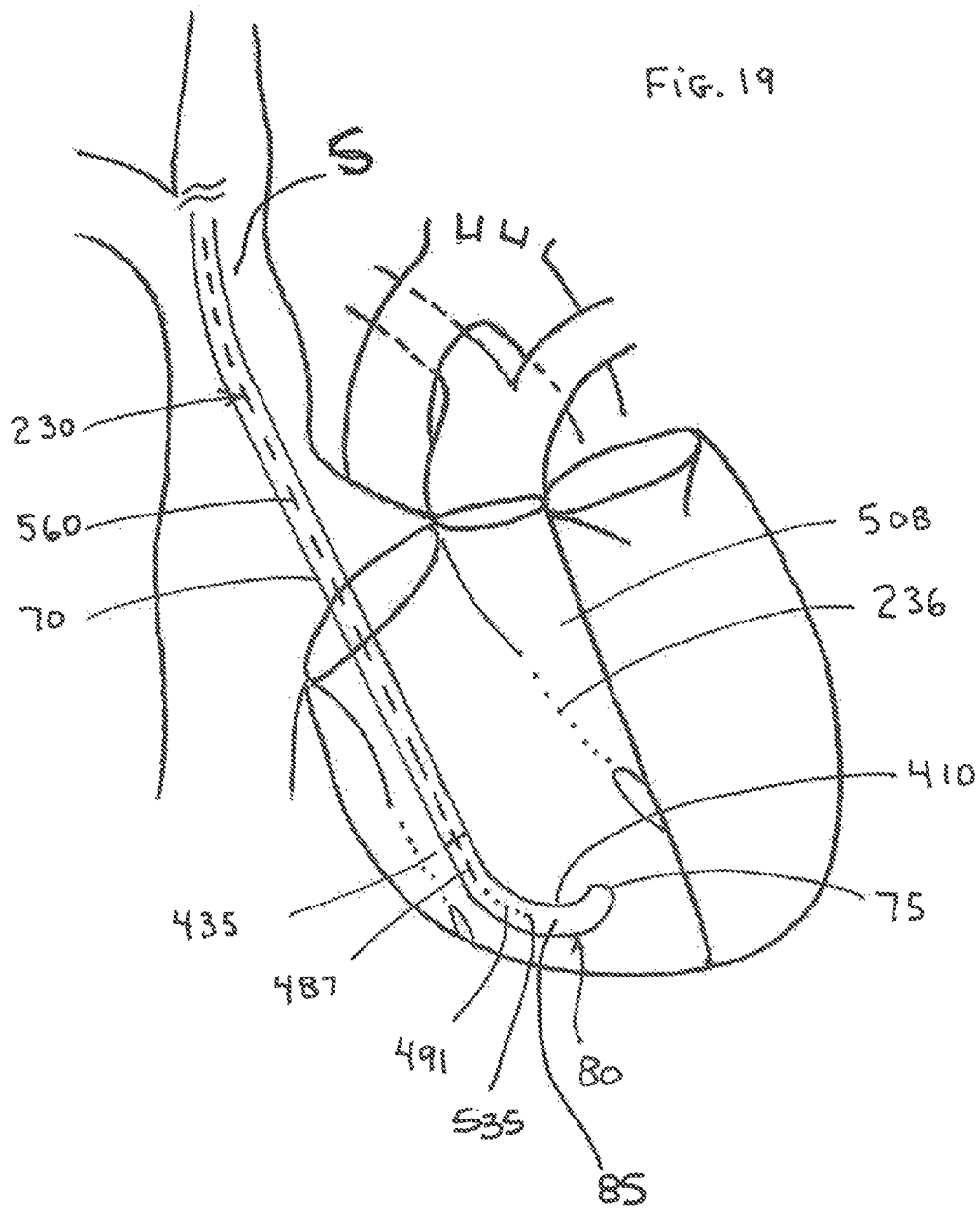

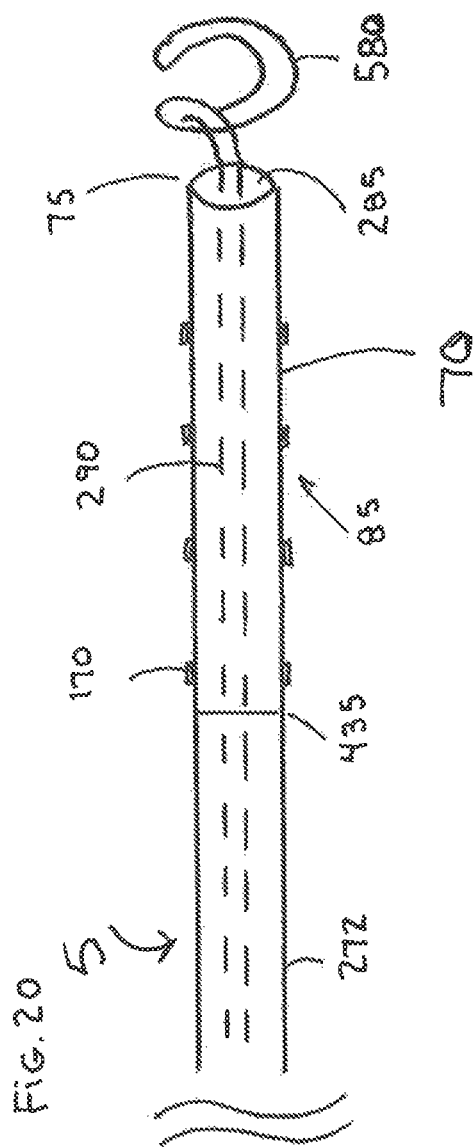

TEMPORARY PACING LEAD

CROSS REFERENCE TO RELATED APPLICATIONS

This patent application is a continuation to U.S. patent application Ser. No. 17/004,520, entitled "Temporary Coiled Pacing Lead," filed Aug. 27, 2020 issued U.S. Pat. No. 11,642,518 which is a continuation of U.S. patent application Ser. No. 15/642,084, entitled "Temporary Pacing Lead," filed Jul. 5, 2017, issued U.S. Pat. No. 10,773,076 and U.S. Provisional Application Ser. No. 62/493,490, entitled "Temporary Coiled Pacing Lead," filed 5 Jul. 2016, U.S. Provisional Application Ser. No. 62/495,765 entitled "Temporary Coiled Over the Wire Pacing Lead," filed 23 Sep. 2016, and U.S. Provisional Application Ser. No. 62/602,397, entitled "Temporary Coiled Floppy Distal Pacing Lead," filed 21 Apr. 2017, all of which are incorporated herein by reference in their entirety.

BACKGROUND OF THE INVENTION

Temporary pacing is performed in patients having cardiac arrhythmias as a bridge to permanent pacing or to recovery; temporary pacing also provides prophylactic utility for specific medical procedures including, for example, transcatheter aortic valve replacement (TAVR) procedures. Such arrhythmias can manifest as bradycardia or tachycardia and can result in hemodynamic instability to the patient. Often bradycardia can occur as a result of sinus node dysfunction or atrioventricular block. Acute therapy can be obtained via placement of a temporary lead in the right ventricle (RV); the temporary pacing lead receives an electrically generated signal from an external pulse generator located external to the patient.

Current temporary pacing leads are generally placed via a percutaneous transvenous access, via a direct epicardial placement of the electrode via a surgical access site or transcutaneous using patches placed on the body surface, i.e., skin. The pacemaker lead can be a unipolar lead with the negative or cathode electrode located at or near its distal end; alternately, the lead can be a bipolar lead thereby containing both the negative cathode and the positive anode on the lead body separated by a small distance of a few millimeters. The unipolar lead requires that a separate anode be located adjacent the subcutaneous tissue at a remote location located several inches away from the cathode. The unipolar lead provides for a greater ease of capture of the electrical pulse by the myocardium from the pacemaker generator and hence is often used for temporary pacing. The bipolar lead provides a benefit over the unipolar lead for requiring a lower threshold energy to obtain capture and hence has greater application for permanent pacing with a preserved battery life for the implanted pulse generator.

Temporary pacing leads can have active fixation elements such as a distally located screw-shaped electrode that is screwed into the myocardium. Such active fixation can hold the lead in place but is also more difficult to place during implantation and more difficult to remove after a few days. Active fixation leads carry a greater likelihood of myocardial perforation and potential for tamponade. Temporary leads can also have passive fixation such as tines that are designed to be entangled within the trabeculae of the endocardial surface to provide adequate lodging and also can be time-consuming to place. Other temporary leads are more easily and quickly placed without active or passive fixation elements but still require fluoroscopy and are easily dislodged by small movements of the pacing lead in relation to the patient thereby resulting in loss of capture of the electrical stimulus from the pacemaker generator even due to small micro-dislodgements. Temporary pacing leads can also have flow-directed balloons located near the distal end to assist with advancement of the pacing lead in the RV chamber but difficult to adequately position for capture and thus require a significant amount of manipulation under fluoroscopy for optimal positioning; flow-directed balloons are less reliable for providing a preferred location for the pacing lead.

Current temporary pacing leads often have a general linear configuration near the distal region of the lead. A slight curve can be formed into the lead to allow it to lay against the wall of a heart chamber such as the right ventricle (RV). Due to the linear configuration, the distal end of the temporary lead can be traumatic to the heart wall and can protrude, penetrate, or perforate through the wall of the heart leading to potential tamponade and which can lead to death of the patient. Placement of such linearly configured leads is performed under fluoroscopic guidance in order to position the lead properly against the endocardial surface of the heart and to prevent inadvertent perforation of the heart wall.

Due to the general linear configuration of standard temporary leads, the distal region of the lead does not easily maintain a position adjacent to the endocardial surface which is needed to maintain sustained electrical capture of the myocardial tissue. Instead the distal region of the lead can easily dislodge and lose capture shortly following placement. The proximal shaft of such a linearly-configured temporary lead is often secured with sutures and adhesive dressing near its manifold to the patient's tissue near the access site to help prevent dislodgement of the lead and loss of capture, however patient movement and inherent motion of the heart tend to easily result in dislodgement of the lead and resultant loss of capture. If the temporary pacing lead should need to be repositioned due to lack of capture as a result of dislodgement, care must be taken and once again requires the use of fluoroscopy, to ensure that the pacing lead does not perforate the myocardial tissue during repositioning. This often requires patient transfer back to the cardiac catheterization laboratory.

Vascular access is obtained via a percutaneous transvenous site through which the temporary pacing lead is performed under fluoroscopic guidance. The lead can be provided percutaneous access using the femoral vein (FV), subclavian vein (SCV), the internal jugular vein (UV), or other suitable venous access sites. The lead is then advanced through the right atrium (RA) and into the RV. The bipolar lead has a negative electrode or cathode and adjacent positive electrode or anode which are found on the distal segment of the lead positioned to obtain adequate contact with the myocardium of the RV such that the electrical pulse from the pulse generator is transmitted to and captured by the myocardium. Radiation exposure while using fluoroscopy can be detrimental to a patient.

Several complications exist during the placement and operation of temporary pacemaker leads; such complications include myocardial damage, generation of arrhythmias, perforations of the myocardium, tamponade, trauma to the tricuspid valve, and dislocation or dislodgement of the pacing lead with loss of capture. Many of the pacer leads are traumatic and their distal end, wherein the electrodes are located, can penetrate the myocardial tissue or perforate the atrial or ventricular wall of the heart.

What is needed is a temporary pacing lead that is easily placed and is atraumatic to the myocardial tissues of the heart including the tissues of the RA and RV. The lead should be placed without the need for fluoroscopy and its associated inconvenience, time, and radiation, also preferably without the need for echocardiographic guidance. The lead should be configured such that more than one cathode and anode is positioned on the lead such that positioning of the lead does not require precise visualization as required by current standard leads which are placed using fluoroscopy. The lead should not be easily dislodged once it is placed in the RV; the lead should be easily stabilized or held in a stationary position in relation to the access sheath such that dislodgements and loss of capture is reduced. If the lead is displaced, it should be easily repositioned without the need for fluoroscopy or ventricular capture preserved with the use of other electrode pairs in a bipolar configuration or using a monopolar option. The temporary pacing lead should be easily removed following the return of a stable patient rhythm or placement of a permanent pacemaker.

SUMMARY OF THE INVENTION

The present invention is directed to a temporary pacing lead that overcomes the objections found in current standard temporary pacing leads. The pacing lead can be used in any of the four chambers of the heart. Often however, the pacing lead is placed into the right ventricle (RV) and hence the discussion presented will focus on this chamber of the heart.

The present invention is specifically directed to a pacing lead for temporary atraumatic placement on a wall surface of a chamber of an animal body part, which can be the endocardial surface of a cardiac chamber, to deliver an electrical signal comprising a lead manifold located outside the animal body; and a pacing lead body connected to the lead manifold, the pacing lead body having a proximal end and a distal end, wherein the pacing lead body comprises a curled shaft having a distal and a proximal end which can be achieved in one embodiment with catheter-shaped memory and a shaped curved memory, wherein the curled shaft is located in the distal end of the pacing lead body for placement of the lead body against the surface of the body part. The curled shaft further includes a plurality of cathode sites, which cathode sites are connected via electrical continuity such that at least one of the plurality of the cathode sites is adapted to be temporarily connected to the wall surface.

The present invention is further directed to a pacing lead for temporary atraumatic placement on a wall surface of a chamber of an animal body part, which can be the endocardial surface of a cardiac chamber, to deliver an electrical signal comprising a lead manifold located outside the body; a pacing lead body connected to the lead manifold, the pacing lead body having a proximal end and a distal end, wherein the pacing lead body comprises: a curled shaft having a distal end and a proximal end, which can be achieved in one embodiment with catheter-shaped memory and an outward memory force, wherein the curled shaft is located in the distal end of the pacing lead body for placement of the lead body against the surface of the body part, the curled shaft further including a plurality of cathode sites, which cathode sites are connected via electrical continuity such that at least one of the plurality of the cathode sites is adapted to be temporarily connected to the wall surface, wherein the cathode sites are connected to a cathode connecting wire extending along the pacing lead body to a cathode connector on the lead manifold, wherein the cathode connector is connected via the cathode connecting wire to a negative pole of a pulse generator, wherein the pulse generator provides voltage and current to the plurality of cathode sites, and an internal lumen having a proximal end and a distal end for receiving a placement stylet; and an introducer sheath to assist in the placement of the pacing lead within the chamber, wherein the introducer sheath comprises an inner surface and an outer surface, wherein the pacing lead is adapted to extend distally through the introducer sheath, wherein the introducer sheath includes an anode site positioned of the outer surface of the introducer sheath, and wherein the anode site is electrically coupled to a temporary pulse generator.

The present invention is further directed to a pacing lead for temporary atraumatic placement on a wall surface of a chamber of an animal body part to deliver an electrical signal. The pacing lead comprises a lead manifold located outside the animal body; a pacing lead body connected to the lead manifold, the pacing lead body having a proximal end and a distal end. The pacing lead body comprises a curled shaft having a distal end and a proximal end, a shaped curved memory and an outward memory force, wherein the curled shaft is located in the distal end of the pacing lead body for placement of the lead body against the surface of the body part, the curled shaft further including a plurality of cathode sites, which cathode sites are connected via electrical continuity such that at least one of the plurality of the cathode sites is adapted to be temporarily connected to the wall surface, wherein the cathode sites are connected to a cathode connecting wire extending along the pacing lead body to a cathode connector on the lead manifold, wherein the cathode connector is connected via the cathode connecting wire to a negative pole of a pulse generator, wherein the pulse generator provides voltage and current to the plurality of cathode sites, and an internal lumen having a proximal end and a distal end for receiving a placement stylet. The pacing lead further comprises an introducer sheath to assist in the placement of the pacing lead within the chamber, wherein the introducer sheath comprises an inner surface and an outer surface, wherein the pacing lead is adapted to extend distally through the introducer sheath, wherein the introducer sheath includes an anode site positioned of the outer surface of the introducer sheath, and wherein the anode site is electrically coupled to a temporary pulse generator; and a control fiber connected to the lead body distal end, wherein the control fiber traverses external to the lead body distal region, wherein the lead body includes a control fiber opening at the proximal of the curled shaft, wherein the control fiber extends through the control opening into a control fiber lumen within the lead body to the lead manifold at the proximal end of the lead body, wherein the lead manifold includes a holding-tensioning member for securing the control fiber and providing tension to the control fiber.

The present invention is further directed to method of temporarily and atraumatically placing a pacing lead on a wall surface of a chamber of an animal body part, wherein the pacing lead comprises a lead manifold located outside the animal body, and a pacing lead body connected to the lead manifold, the pacing lead body having a proximal end and a distal end. The pacing lead body comprises a curled shaft having a distal end and a proximal end and a shaped curved memory, wherein the curled shaft is located in the distal end of the pacing lead body for placement of the lead body against the surface of the body part, the curled shaft further including a plurality of cathode sites, which cathode sites are connected via electrical continuity such that at least one of the plurality of the cathode sites is adapted to be temporarily connected to the wall surface, and an internal lumen having a proximal end and a distal end for receiving a placement stylet. The method comprises the following steps: (a) slidingly advancing the stylet within the internal lumen toward the distal end of the lead body of the pacing lead to cause the lead distal region to form a generally linear shape; (b) advancing the pacing lead through the introducer sheath toward the chamber of the animal body part; (c) holding the stylet in a fixed position and advancing the pacing lead distally into the chamber; (d) slidingly removing the stylet from the distal end of the lead body of the pacing lead, such that the distal end initiates the formation of the curled shaft within the chamber; and (e) advancing the temporary pacing lead further while maintaining the stylet at a fixed position to allow the lead distal end to form an equilibrium configuration of a curved loop.

The present invention is further directed to a method of temporarily and atraumatically placing a pacing lead on a wall surface of a chamber within an animal body part, wherein the pacing lead comprises a lead manifold located outside the animal body part, and a pacing lead body connected to the lead manifold, the pacing lead body having a proximal end and a distal end. The pacing lead body comprises: a curled shaft having a distal end and a proximal end and a shaped curved memory, wherein the curled shaft is located in the distal end of the pacing lead body for placement of the lead body against the surface of the body part, the curled shaft further including a plurality of cathode sites, which cathode sites are connected via electrical continuity such that at least one of the plurality of the cathode sites is adapted to be temporarily connected to the wall surface, an internal lumen having a proximal end and a distal end for receiving a placement stylet, and a control fiber connected to the distal end of the pacing lead body, wherein the control fiber traverses external to the pacing lead body distal region, wherein the lead body includes a control fiber opening at the proximal end of the curled shaft, wherein the control fiber extends through the control opening into a control fiber lumen within the pacing lead body to the lead manifold at the proximal end of the pacing lead body, wherein the lead manifold includes a holding-tensioning member for securing the control fiber and providing tension to the control fiber. The method comprises the following steps: (a) placing the pacing lead body in a linear configuration to traverse an introducer sheath; (b) introducing a stylet into the internal lumen; (c) providing sufficient tension to the control fiber from the lead body distal end to the control opening to provide a lead loop controlled radius of curvature to the lead distal region of the curled shaft; (d) traversing the lead body distal end of the lead body to the chamber; (e) applying tension to the control fiber via the holding-tensioning member thereby causing the lead body distal region to form a closed loop having a lead loop controlled radius of curvature sufficient to allow entry of the distal end of the pacing lead body into the chamber in an atraumatic manner; and (f) releasing the tension of the control fiber to enable the lead distal region to form the curled shaft having an open loop.

The curled shaft of the present invention contains at least one and preferably a plurality of cathode sites all of which are connected together via electrical continuity to form a single cathode or cathode electrode which characterizes the present temporary pacer lead as a unipolar lead. The plurality of cathodes sites allows the present unipolar temporary pacing lead to be easily placed within the chamber of the heart such that at least one of the cathodes sites is in contact with a region of the endocardium to create a capture site that is needed to temporarily pace the heart. The curled shaft applies a small outward force onto two opposing walls of the heart chamber and hence place the cathode sites into contact with the endocardial surface of the myocardium to ensure electrical contact and capture of the pacing signal from the pulse generator.

Due to this multiplicity of cathode sites and combined with the atraumatic shape of the distal curled region, the pacer lead of the present invention can be placed without fluoroscopic imaging or possibly under echo guidance without the concern for perforation of the heart wall while ensuring that at least one of the cathode sites is creating an electrical capture of the myocardium for temporary pacing. Placement of the pacing lead will not require the fluoroscopic guidance since the curled distal region with the multiplicity of cathode sites does not require the visualization provided by fluoroscopy as required by standard leads to reduce the likelihood for pacing lead perforations and ensure precise placement for standard temporary pacing leads. Confirmation of proper placement of the curled distal region into the RV can be guided by echo.

This temporary pacing lead embodiment of the present invention has a unipolar cathode electrode rather than a bipolar electrodes placed on the lead body. The unipolar cathode allows the present invention to provide capture of the electrical pulse signal by the myocardium easier than a bipolar electrode due to the ability to provide a larger current density required to reach a capture threshold. For temporary pacing, the ease of myocardial capture is of greater importance than the lower capture threshold found in bipolar leads and needed to conserve battery power for a permanent pacemaker. The ease of capture combined with the ability to capture with any of the multiplicity of cathode sites provides the multiple unipolar cathode sites of the present invention with an advantage over other pacing leads to provide an even greater ease and consistency of capture.

Placement of the temporary pacing lead of the present invention may be performed by first placing a placement stylet or guidewire into an internal lumen of the pacing lead. The stylet, for example, may have a linear or curved shape that does not form a closed loop; the stylet has a radius of curvature that may be much larger than the radius of curvature of the closed loop of coiled shaft of the temporary pacing lead of some embodiments of the present invention. Placement of the stylet into the lumen of the pacing lead causes the distal coiled shaft of the pacing lead to form a more gently curved shape that allows the pacing lead to traverse the venous vasculature to the heart and cross the tricuspid valve (TCV) annulus. The distal end of the pacing lead can be a closed end such that the stylet is able to extend within the internal lumen of the pacing lead but cannot extend distally beyond the closed distal end. Once the pacing lead is across the TCV, the pacing lead can be advanced into the heart chamber where the distal region of the pacing lead can form a distal curled region within the RV. The pacing lead can be advanced under echo guidance to place the distal curled region into contact with the lateral wall, apex, and septal wall of the RV. The distal curled region has a radius of curvature that is similar to the endocardial surface of the chamber of the heart and hence it confers an atraumatic character.

In another embodiment the pacing lead can have an open distal end such that the pacing lead can pass over a floppy coiled guidewire that has been placed through the vasculature and into the right ventricle. This atraumatic guidewire would have a softer curved shape located within the chamber of the right ventricle and a stiffer and straighter shaft located within the right atrium and venous vasculature extending from the access site to the heart. The pacing lead of this embodiment can then be advanced over the wire into the right ventricle and around the coiled wire positioned in the right ventricle in a safe and atraumatic manner.

To assist in placing the lead into the RV under hemodynamic guidance, a distal orifice or orifices can be placed in the distal region of the coiled shaft at a location distal to the cathode sites. The orifices connect to a fluid-filled lumen enabling delay of pressure waveform when connected to a pressure transducer characteristics of the chamber in which it rests. Again, observation of the pressure signal within the blood vessel or chamber via a pressure transducer that is sealingly connected to the manifold pressure port provides the operator with a distinguishing pressure that is characteristic of the location of the distal region of the pacing lead thereby giving knowledge of the location of the distal region of the pacing lead to the operator. The side or end orifices can also be used for delivery of contrast medium or for delivery of a drug to the central (intracardio) circulation via the manifold port when it is connected, for example to a syringe.

If the pacing lead becomes dislodged at a later time period other than the initial lead placement setting, the pacing lead can be easily and safely repositioned to regain capture possibly under hemodynamic guidance without concern for lead perforation through the heart wall. Due to the curled atraumatic distal region and the multiplicity of cathode sites, a small adjustment of the pacing lead either via distal or proximal movement of the pacing lead body will result in electrical recapture of the myocardial via any one of the electrode sites found in the curled distal region. Repositioning of the pacing lead can occur either blindly or with hemodynamic echocardiographic or, if absolutely necessary, fluoroscopic guidance.

In one embodiment an echogenic coating is applied to the pacing lead body and to the distal coiled region of the pacing lead. The echogenic coating can aid in visualizing the pacing lead under echo guidance during initial placement or repositioning of the pacing lead. Portable echocardiographic image can be easily performed transthoracically at the bedside.

In another embodiment the anode of the present invention is provided as a component of the introducer sheath that provides passage for the temporary pacing lead at the access site into the vasculature of the body. The anode can be positioned as a portion of the outer surface of the introducer sheath in contact with adjacent soft tissue overlying the vascular entry site. This then can be electrically coupled to the temporary pulse generator. Alternately, the anode can be attached to the introducer sheath as a sticky patch electrode or a sticky flange electrode that is placed into contact with the subcutaneous tissue at the access site into the venous vasculature. A locking screw can also be located on the introducer sheath near the manifold to tighten down on the pacing lead and fix the lead position to avoid inadvertent lead migration within the heart that can result in loss of electrical capture.

Advantages are provided by a loop configuration for the coiled region of the temporary pacing lead including atraumatic contact with the myocardial wall and providing an outward force on the multiplicity of electrodes against the two opposing endocardial walls of the heart chamber to attain consistent capture of the electrical stimulation signal. Most embodiments of the present invention are not required to have a closed loop configuration in order to provide atraumatic contact with the myocardium and maintain effective and stable capture. An open loop distal can have numerous shapes and sizes to maximize good position on multiple sites. Such other embodiments without a closed loop provided by the embodiment with different shapes and sizes give the additional advantage for removal of the pacing lead from the heart chamber without potential for entanglement and potential disruption of cordae tendineae which would create an incompetent TV. The distal region of the curled shaft that forms the curled loop is formed with a low bending modulus material such that the curled loop is easily bent during removal of the pacing lead, still minimizing this risk.

The objects and advantages of the invention will appear more fully from the following detailed description of the preferred embodiment of the invention made in conjunction with the accompanying drawings.

BRIEF DESCRIPTION OF THE DRAWINGS

FIG. 1B is a plan view of a curled temporary pacing lead with an open loop.

FIG. 1C is a cross-sectional top view of the introducer sheath manifold and pacing lead manifold showing a sheath indicator and lead indicator to provide the ability to appropriately orient pre-curved distal catheter.

FIG. 2 is a plan view of a temporary pacing lead showing the multiplicity of cathodes in the distal region and their connection to the cathode conduction wire.

FIG. 3A is a plan view showing the distal region of a temporary pacing lead with a small overlap portion for the coiled shaft of a closed loop with a round shape.

FIG. 3B is a plan view showing the distal region of a temporary pacing lead with a large overlap portion for the coiled shaft of a closed loop with an oval shape.

FIG. 3C is a plan view showing the distal region of a temporary pacing lead with a large overlap portion for the coiled shaft of a closed loop.

FIG. 4 is a plan view showing the distal region of a temporary pacing lead with an echogenic coating located on the outer surface of the coiled shaft.

FIG. 6 is a plan view of a temporary pacing catheter entering the heart chamber over a stylet within the central lumen.

FIG. 7A is a plan view of temporary pacing lead with a stylet in the lead central lumen and extending to the distal end of the lead.

FIG. 7B is a plan view of temporary pacing lead with a stylet in the lead central lumen and having the stylet retracted to allow the lead distal region to form a curled shaft.

FIG. 8B is a partially perspective view of a temporary pacing lead with an open distal end advancing over a guidewire to the heart apex.

FIG. 8C is a partially perspective view of a temporary pacing lead with an open distal end advancing over a guidewire to form a closed loop.

FIG. 9A is a plan view of a temporary pacing lead having an open distal end and showing a guidewire passing through the lead central lumen.

FIG. 9B is a plan view of a temporary pacing lead having an open distal end and showing a guidewire being retracted to allow the lead distal region to form a closed loop.

FIG. 11 is a plan view of a temporary pacing lead that is a bipolar lead that has a multiplicity of both cathode electrodes and anode electrodes in the curled shaft.

FIG. 12C is a plan view of a distal region of a temporary pacing lead showing a lead equilibrium loop angle of 270 degrees.

FIG. 12D is a plan view of a distal region of a temporary pacing lead showing a lead equilibrium loop angle of 90 degrees.

FIG. 12E is a plan view of a distal region of a temporary pacing lead showing a lead equilibrium loop angle of zero degrees.

FIG. 13H is a cross-sectional top view of a lead manifold and stylet manifold showing a lead indicator and stylet indicator to provide alignment of the lead and the stylet.

FIG. 14A is a partial perspective view of a temporary pacing lead located in the apex of the heart with a removal stylet inserted in the lead central lumen to assist with removal of the pacing lead.

FIG. 14B is a plan view of a proximal region, distal region, and distal tip of a removal stylet.

FIG. 15A is a plan view of a proximal region and distal region of a vascular stylet.

FIG. 15B is a plan view of a distal region of a lead equilibrium loop of a temporary pacing lead.

FIG. 15C is a plan view of the pacing lead proximal and distal region having a vascular stylet inserted into the lead central lumen.

FIG. 16A is a plan view of a ventricular placement stylet.

FIG. 16B is a plan view of a lead distal region forming a lead equilibrium loop upon partial retraction of the ventricular placement stylet.

FIG. 16C is a plan view of a ventricular placement stylet having a stylet curled shaft.

FIG. 16D is a plan view of a lead distal region having a ventricular placement stylet inserted into the lead central lumen to form a lead-stylet radius of curvature.

FIG. 17 is a partially perspective view of a temporary pacing lead entering the heart annulus and also a view of the temporary pacing lead advanced into the heart apex and having an lead loop equilibrium radius of curvature.

FIG. 18 is a partially perspective view of a temporary pacing lead located in the heart apex and having a pacing stylet inserted into the lead central lumen to enlarge the radius of curvature to a lead-stylet radius of curvature to contact two walls of the heart chamber.

FIG. 19 is a partially perspective view of a temporary pacing lead located in the heart apex and having a removal stylet inserted into the lead central lumen to assist with removal of the lead from the heart chamber, preventing sub-tricuspid valve apparatus entanglement.

FIG. 20 is a perspective view of a lead distal region having a guidewire with a spiral loop or pig tail extending of the lead open distal end and allowing the lead and guidewire to be advanced safely into the heart chamber without echo guidance or fluoroscopic guidance.

DETAILED DESCRIPTION OF THE INVENTION

Figure 1A:
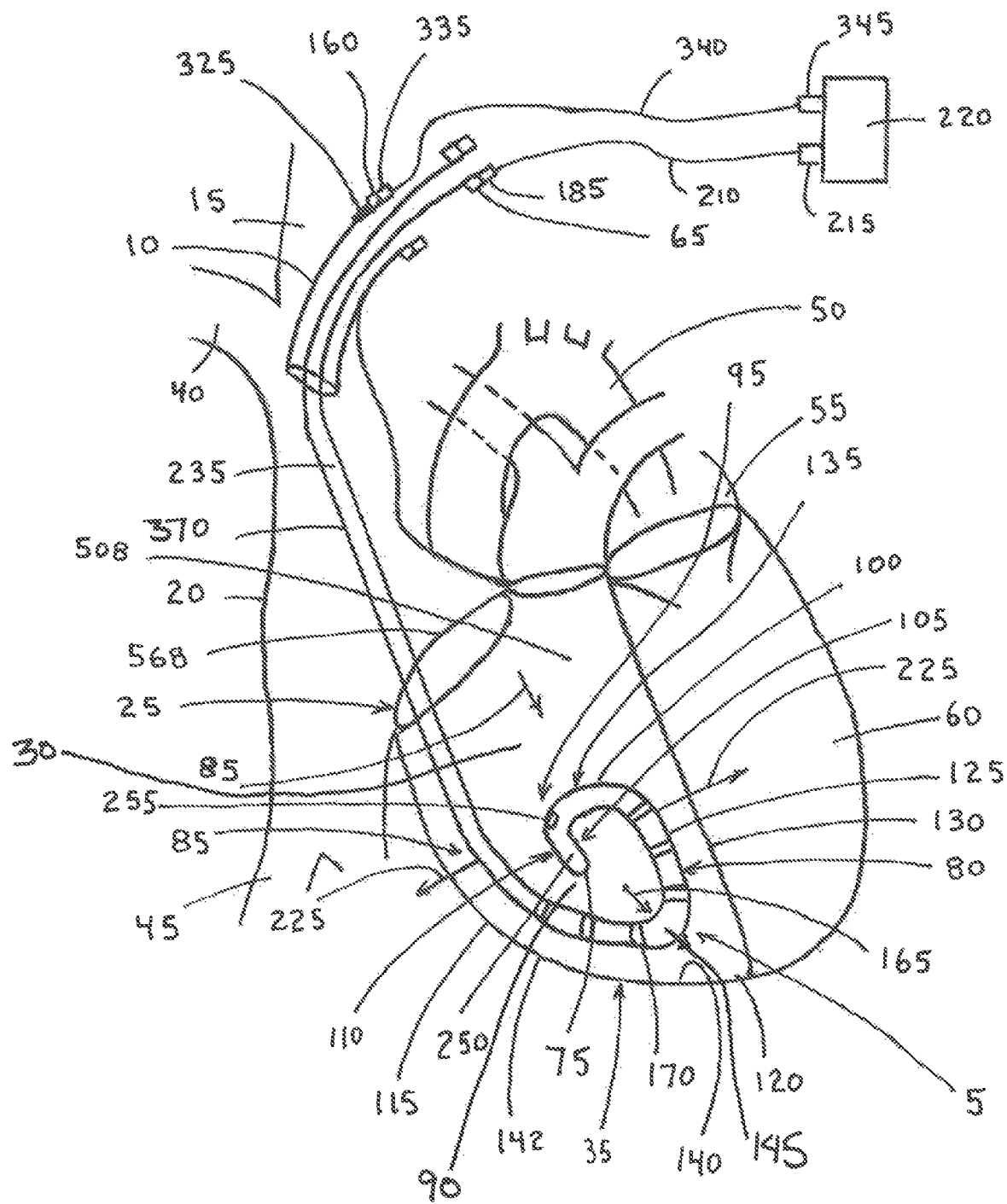
FIG. 1A is a partially perspective plan view of a curled temporary pacing lead with a closed loop having a multiplicity of cathode electrodes in the right ventricle of the heart.

FIG. 1A shows an embodiment of the present invention for a temporary pacing lead 5. In this embodiment the pacing lead 5 is introduced through an introducer sheath 10 placed in the internal jugular vein (IJV) 15; the pacing lead 5 extends through the right atrium (RA) 20 and across the tricuspid valve (TCV) 25 and into the right ventricle (RV) 30 of the heart 35. It is understood, however, that this invention applies also to other entry sites into the vasculature including the subclavian vein (SCV) 40, the femoral vein (FV) 45, the aorta 50, or other blood vessels or conduits of the body; the pacing lead 5 can also be used to pace the RA 20, left atrium (LA) 55, left ventricle (LV) 60 or other chambers of the heart 35 or body.

As shown in FIGS. 1A and 2 the pacing lead 5 has a lead manifold 65 located outside of the body, the lead manifold 65 is attached to the lead body 70 which extends distally through the introducer sheath 10. The lead body 70 of the pacing lead 5 extends distally to the lead distal end 75. A curled shaft 80 is formed in the lead distal region 85 of the pacing lead 5. The curled shaft 80 can have an open loop 90 as shown in FIG. 1B or the curled shaft 80 can have a closed loop 95 as shown in FIGS. 1A and 2 (and which can be referred to as a coiled shaft 100, a subgroup of a curled shaft 80). All structures for the coiled shaft 100 are understood to be included into the broader description of a curled shaft 80, and hence reference names and reference numerals used to describe a coiled shaft 100 apply to a curled shaft 80 which includes other embodiments of the present invention described subsequently in the specification.

Curled Shaft 80 and Coiled Shaft 100

The curled shaft 80 comprised of a coiled shaft 100 has been positioned within the RV 30 and is ready for pacing of the RV 30 as shown in FIG. 1A. The coiled shaft 100 forms a closed loop 95 such that there is an overlap portion 105 that overlaps or extends adjacent to and in the same direction as another portion of the coiled shaft 100 to form a coiled or spiral shape and which is referred to herein as a closed loop 95. The curled shaft 80 has a distally directed portion 110 that follows along the lateral wall 115 of the RV 30, for example, and bends to contact or subtend the apex 120 of the heart 35, a proximally directed portion 125 that follows along the septal wall 130 of the RV 30, for example. A closing portion 135 and an overlap portion 105 completes the closed loop 95 of the coiled shaft 100 by coming into near proximity or contact with the distally directed portion 110; the lead distal end 75 does not extend outward into contact with the endocardial surface 140 of the myocardial tissue 142 of the heart 35. Each portion of the coiled shaft 100 extends in a single plane as it forms its coiled or spiral shape. The lead distal end 75 of the pacing lead 5 of this embodiment is located in the overlap portion 105 of the coiled shaft 100 which extends with a radius of curvature that is less than the distally directed portion 110 and does not contact the endocardial surface 140. At least some of the overlap portion 105 extends with a distal direction 145 similar to the distally directed portion 110 to form the closed loop 95. As shown in FIG. 1A the curled shaft 80 can be oriented within the RV 30 chamber such that the plane of the curled shaft 80 extends from the septal wall 130 to the lateral wall 115 or at any other orientation within the ventricular chamber. Orientation can be obtained by positioning a lead indicator 150 located on the lead manifold relative to a sheath indicator 155 located on the sheath manifold 160, for example, as shown in FIG. 1C.

Materials Forming Lead Body 70

The pacing lead body 70 and curled shaft 80 are formed from materials found in existing pacing leads known to the art. An insulative polymer tubing formed from polyurethane or silicone, for example, can be used to form the lead body 70 and curled shaft 80 and retain the curled shape of the curled shaft 80. The profile diameter of the insulative polymer tubing and for the curled shaft 80 is preferably 5 French (Fr) with a range of 4 Fr to 8 Fr. A shaped metal wire can be embedded within the wall of the tubing to assist in forming the curled shape of the curled shaft 80. The shaped metal wire can be formed from Nitinol, Elgiloy, or other elastic material that can help retain the shape of the curled shaft 80. Nitinol (an acronym for Nickel Titanium Naval Ordnance Laboratory) is a family of intermetallic materials, which contain a nearly equal mixture of nickel (55 wt. %) and titanium. Other elements can be added to adjust or "tune" the material properties. These materials are known to exhibit unique behavior, specifically, a well-defined "shape memory" and super elasticity. The curled shaft 80 has a curled shaft radius of curvature 165 of preferably 1-2 cm with a range of about 0.5-3 cm, such that it can traverse the TCV 25 and enter the RA 20 and matches the shape of the apex 120 and mid-cavity of the chamber of the heart 35. The curled shaft radius of curvature 165 for the curled shaft 80 may be larger in the distally directed portion 110 than the proximally directed portion 125; the radius of curvature may become smaller as the curled shaft 80 extends from the distally directed portion 110 to the distal end 75 of the pacing lead 5.

Cathode Sites 170

Located along the curled shaft 80 is a plurality of cathode sites 170 which have electrical continuity with each other; each electrode site is connected electrically via a cathode continuity member 175 to a cathode conduction wire 180 which extends along the pacing lead body 70 to the cathode connector 185 located on the lead manifold 65. Each cathode site 170 can be formed by a ring electrode 190, for example, which is placed around the insulative tubing 195 encircling the curled shaft 80. The ring electrode 190 can be formed from platinum or other metal or metal alloy used to form pacing lead electrodes. The cathode conduction wire 180 can be formed from multi-filer metal coiled wire used in current pacing leads to transmit electrical signals through the lead body 70 and curled shaft 80 to each of the ring electrodes 190 located in the distal region 85 of the pacing lead 5. Construction material for the cathode conduction wire 180 can be of a metal or metal alloy used in pacing leads currently found in the industry. The multiplicity of cathode sites 170 forms a single cathode electrode or cathode 320. The number of cathode sites 170 can range from 2 to 20 and can be located along the distally directed portion 110, the proximally directed portion 125, or other portions of the curled shaft 80. The cathode site spacing 200 between each of the cathode sites 170 or between each ring electrode 190 is enough to ensure that at least one cathode site or ring electrode 190 is able to make contact with the endocardial surface 140 such that capture of the signal from the ring electrode 190 is obtained. The cathode site spacing 200 is set at a distance of preferably 1 cm with a range of 0.5 cm-2 cm. The electrode area 202 of each ring electrode 190 or cathode site is such to provide a current density from the ring electrode 190 to the myocardium that will generate capture of the myocardium. The ring electrode length 205 for each ring electrode is preferably 3 mm with a range of 1 mm-5 mm.

Pulse Generator 220

The cathode connector 185 located on the lead manifold 65 is connected via a cathode connecting wire 210 to the negative pole 215 of a pulse generator 220. The pulse generator 220 provides the voltage and current to the cathode electrode or cathode 320 found in the curled shaft 80 to provide temporary pacing for the patient. Standard pacing currents and voltages are used with the present invention as with standard pacing leads; adjustments can be made to the current to account for appropriate current density found for the multiplicity of cathode sites 170 to obtain appropriate myocardial capture of the electrical signal. When a specified current or voltage is delivered to the cathode 320, the signal is received by the endocardial surface 140 of the myocardial tissue 142 and the electrical signal is transmitted through the myocardial tissue 142; the signal from the cathode 320 has then been captured by the myocardial tissue 142.

Due to the multiplicity of cathode sites 170 contact of any one of the cathode sites 170 with the endocardial surface 140 can result in capture of the electrical signal from the pulse generator 220. The multiplicity of cathode sites 170 allows the pacing lead 5 of the present invention to be positioned more easily within the chamber of the heart 35 since any one of the cathode sites 170 can effectively cause capture to occur.

The coiled shaft 100 located in the lead distal region 85 of one embodiment forms a closed loop 95 that is atraumatic to the patient and will not allow the distal end 75 of the pacing lead 5 to perforate the myocardial tissue 142 since the lead distal end 75 of this embodiment is not placed into contact with the myocardial tissue 142 as found in most of the current standard pacing leads. This atraumatic shape for the distal region 85 combined with the multiplicity of cathodes sites 170 allows the pacing lead 5 to be placed without fluoroscopic guidance or echo guidance due to the atraumatic shape of the distal region 85. The present pacing lead 5 ensures a successful capture since the instant pacing lead 5 can obtain capture via any one of the multiplicity of cathode sites 170. Echo guidance may be used primarily to assist with placement and assess lead positioning. Fluoroscopy is required for placement of present standard pacing leads to ensure that the pacing lead 5 lies along the endocardial surface 140 without perforation and for more precise positioning to obtain capture.

The curled shaft 80 found in the distal region 85 of the pacing lead 5 of the present embodiment also helps to provide an outward curled shaft applied force 225 to place the cathode sites 170 into intimate contact with the endocardial surface 140 of the heart 35. The distally directed portion 110 of the curled shaft 80 and the proximally directed portion 125 of the curled shaft 80 helps to place an equal and opposite outward lead curled shaft applied force 225 onto two opposing walls of the RV chamber of the heart 35. The outward curled shaft applied force 225 pushing the curled shaft 80 against the endocardial tissues helps to ensure capture of one of the cathodes sites 170 with the myocardium and prevent dislodgement of the cathode site 170 from their lodging adjacent to the myocardial tissue 142.

In the circumstance that the cathode site 170 becomes dislodged at a later time period following the insertion of the temporary pacing lead 5, the pacing lead 5 of the present invention is easily repositioned without the need for fluoroscopy and also without the need for echo guidance. Due to the curled-shaped distal region 85 and the multiplicity of cathode sites 170, a small advancement of the lead body 70 in a distal direction 145 or retraction proximally will allow the previously captured cathode site 170 or a new neighboring cathode site 170 (or second cathode site) to make contact with the endocardial surface 140 and regain capture.

Shapes of the Curled Shaft 80

Various shapes for the curled shaft 80 have been contemplated; the curled shaft 80 can form a shape that approximates the internal endocardial surface 140 of the heart chamber 508. As shown in FIGS. 3A-3C, the curled shaft 80 can be a coiled shaft 100; the amount of overlap portion 105 can involve only the distal end 75 of the pacing lead 5 as shown in FIG. 3A or the overlap portion 105 can include a spiral that continues at a smaller radius of curvature as shown in FIG. 3C. The curled shaft 80 can be oval shaped as shown in FIG. 3B or can be more rounded as shown in FIG. 3C. The curled shaft 80 can also be formed without an overlap portion 105 as discussed in later embodiments.

Echogenic coating 226 can be applied to the outer surface 228 of the lead body 70 and lead distal region 85 as shown in FIG. 4 to enhance its ability to be visualized on echo guidance. For example microspheres can be adhered to or embedded into the outer surface 228 of the pacing lead 5 to reflect sound waves and enhance visualization. Alternately, echogenic materials that absorb, reflect, or generate sound waves can be located on the outer surface 228 of the pacing lead body 70 or lead distal region 85.

Placement of Temporary Pacing Lead 5

Figure 5:
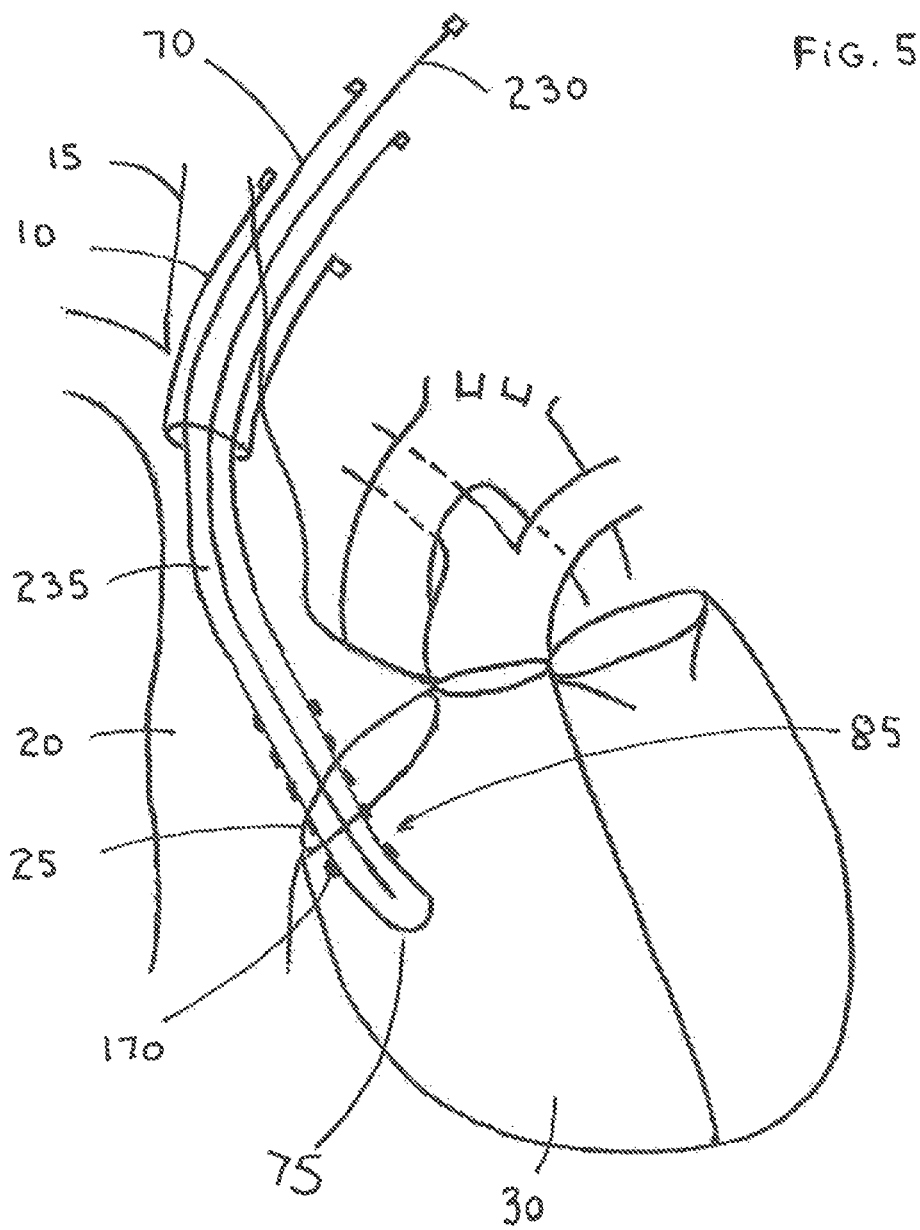
FIG. 5 is a plan view of a temporary pacing catheter crossing the heart annulus with a stylet contained in the central lumen.

Placement of the temporary pacing lead 5 of the present invention under echo guidance or without echo guidance is shown in FIGS. 5 and 6 with the final placement as shown in FIG. 1A. As seen in FIG. 5, a linearly-shaped wire or probe such as a stylet 230, for example, is slidingly placed within the lead central lumen 235 to cause the lead distal region 85 to form a generally linear shape. The radius of curvature for the distal region 85 with the stylet 230 inserted is greater than 10 cm. The stylet 230 is formed from a metal such as stainless steel, Nitinol, or other metal or composite and has a linear shape with a radius of curvature greater than 10 cm. The pacing lead 5 with the stylet 230 inserted is advanced through the introducer sheath 10 located in the internal jugular vein, IJV 15 along with the stylet 230 and across the tricuspid valve 25. A transthoracic echo (TTE) probe can be used to view the passage of the pacing lead 5 and stylet 230 across the TCV 25 as shown in FIG. 5.

While holding the stylet 230 in a fixed position, the pacing lead 5 is advanced distally into the right ventricle, RV 30. With the stylet 230 no longer located in the distal region 85, the distal region 85 initiates the formation of a curled shaft 80 that extends into the RV as shown in FIG. 6. The curled shaft 80 has a curled shaft radius of curvature of preferably 1 cm with a range of 0.5-3.0 cm to fit within the TCV 25 and not snag the cordae tendineae 236 of the heart valve 238. The lead distal end 75 of this embodiment has a closed distal end 240 that is a blunt rounded surface with no lead central lumen 235 extending therethrough and does not allow the stylet 230 or a stiff guidewire 290 to extend out of the lead distal end 75. Further advancement of the pacing lead 5 while holding the stylet 230 at a fixed position allows the lead distal region 85 to form an equilibrium configuration of a closed loop 95 as shown in the coiled region of FIG. 1A or an open loop 90 as shown in FIG. 1B.

FIGS. 7A and 7B show an embodiment for the pacing lead 5 of the present invention having one or more orifices 245 located in the distal region 85 of the curled shaft 80, i.e., between the lead distal tip 250 and the distal region 85 not containing the cathode sites 170. The orifices 245 can be one or more side orifices 255 as shown in FIGS. 7A and 7B which extends through the curled shaft wall 260 and is in direct fluid communication with the lead distal lumen 265. The distal lumen 265 forms a portion of the central lumen 235 that extends throughout the lead body 70 of the pacing lead 5. The one or more orifices 245 should be smaller than the stylet diameter 266 to contain the stylet 230 within the distal lumen 265 but should provide a hydraulic diameter, i.e., a calculated diameter that is equivalent hydraulically to the distal lumen diameter 275, that does not dampen a pressure signal from the blood from an outside region 268 outside of the curled shaft 80 to the distal lumen 265 of the pacing lead 5. A manifold port 270 located on the lead manifold 65 is also in direct fluid communication with the lead central lumen 235 of the lead body 70. A pressure transducer (not shown) can thereby be sealingly connected to the manifold port 270 and detect a pressure signal from the body fluid or blood that is located on the outside of the curled shaft 80 in the lead distal region 85 of the catheter body adjacent to the side orifice 255. The operator can use the characteristic of the pressure signal which varies from the RA 20 to the RV 30, for example, to determine the location of the lead distal region 85 while the pacing lead 5 is being delivered through the vasculature and into the heart chambers 508. Identification can be made by the operator that the lead distal region 85 has been delivered to the RV 30. Thus, the pacing lead 5 can be delivered to the RV 30 without using fluoroscopy if desired, and can be delivered under echo guidance, if desired, with the added assistance of observing the pressure signal that is characteristic of the desired delivery location for the distal region 85 within the heart 35 and vasculature. This establishes the opportunity to deliver the lead under hemodynamic guidance.

The location of the side orifice 255 or orifices 245 should be distal to the cathode sites 170 such that the pressure signal that is received from the operator indicates the pressure of the chamber into which the operator is entering, such as the RA 20 or RV 30, for example. Also, as shown in FIGS. 1A and 7B, the side orifice 255 or other pressure sensing orifices 245 should be located in the lead distal tip 250 such that as the curled shaft 80 is located in the ventricular chamber such as the RV 80, the orifices 245 are positioned closer to the right atrium 20 and closer to the lead proximal region 272 than are the cathode sites 170 positioned to ensure that the cathode sites 170 are correctly and safely located near the apex 120 of the heart 35.

As shown in FIG. 7A, the stylet 230 can be placed within the lead central lumen 235 to allow ease of delivery of the pacing lead 5 through the vasculature as described in FIGS. 5 and 6. During the delivery of the pacing lead 5 and after achieving a final location for the pacing lead 5 within the RV 30, the operator can partially withdraw the stylet 230 out of the lead distal region 85. The distal lumen 265 then becomes available for pressure signal transmission back to the manifold port 270. The distal lumen diameter 275 needed to deliver the pressure signal without degradation or dampening of the pressure signal intensity is preferably 0.020 inches with a range 0.016-0.030 inches. The stylet 230 can reside in the proximal lumen 280 of the lead body 70 during pressure signal transmission; the proximal lumen 280 is a portion of the central lumen 235 that resides within the lead proximal region 272 of the lead body 70 and is located proximal to the curled shaft 80. The annular space between the lead body 70 and the stylet 230 must provide a hydraulic diameter (i.e., a calculated diameter that is equivalent hydraulically to the distal lumen diameter 275) that is equal or greater than the distal lumen diameter 275. Alternately, the stylet 230 can be pulled back out of the central lumen 235 such that the stylet 230 does not provide any reduction in area in the central lumen 235 that could be used for pressure signal transmission; such reduction in central lumen area could result dampening of the pressure signal that is being transmitted from the side orifice 255 to the manifold port 270.

Figure 8A:
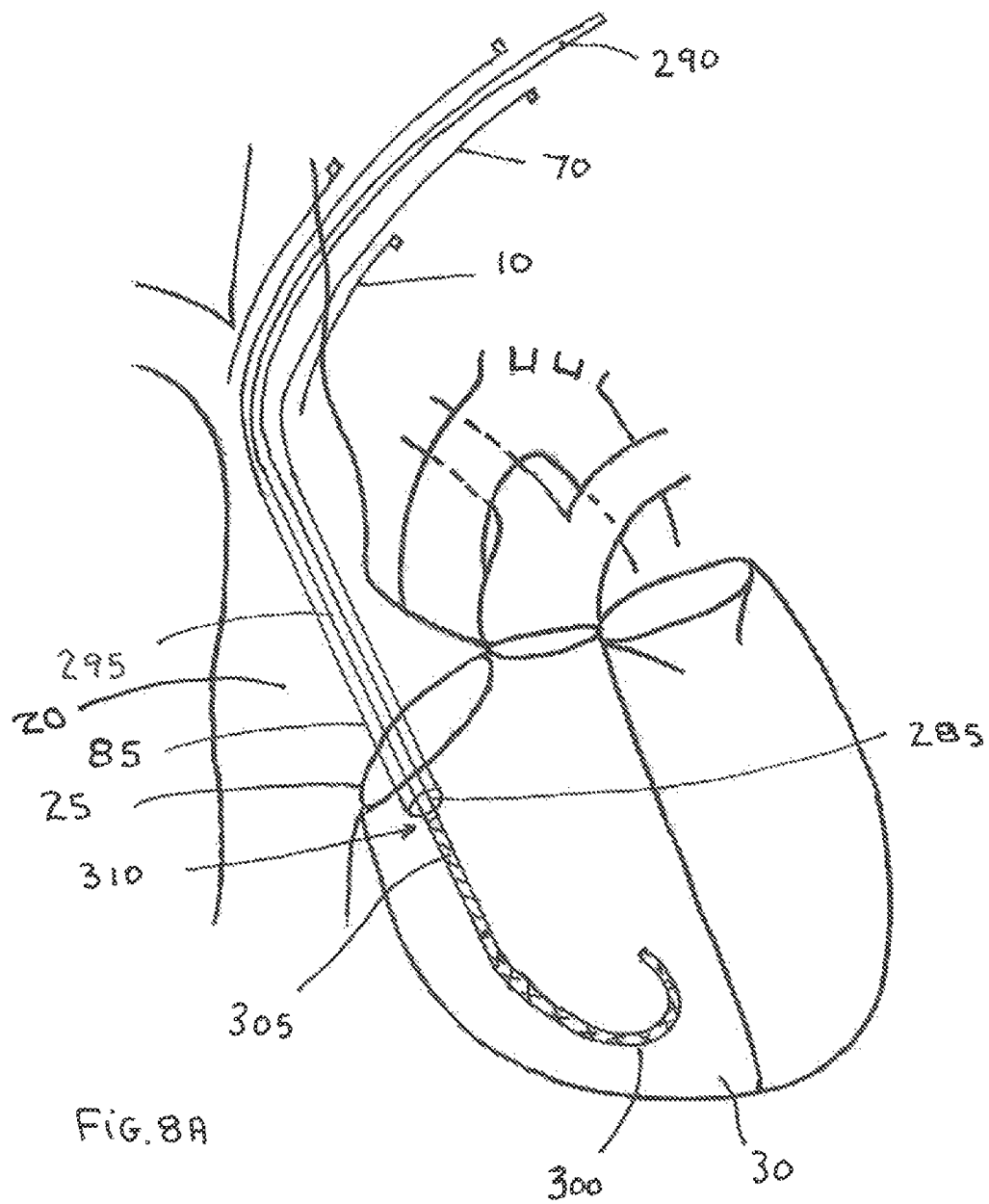
FIG. 8A is a partially perspective view of a temporary pacing lead with an open distal end entering the heart chamber over a guidewire with a distal floppy end.

Alternate Embodiment—FIGS. 8A-8C

An alternate embodiment for the pacing lead 5 of the present invention has an open distal end 285 as shown in FIGS. 8A-8C. As shown in FIG. 8A a stylet 230 such as a guidewire 290, for example, is first placed through the introducer sheath 10 and into the RV 30. The guidewire 290 can have a guidewire stiff region 295 that is located within the introducer sheath 10 and extending across the TCV 25. The guidewire stiff region 295 is intended to interface with the lead distal region 85 during delivery of the pacing lead 5 through the vasculature such that the lead distal region 85 becomes more linear or less curved, i.e., less curled, and can traverse the vasculature more easily to reach the RV of the heart 35. A softer guidewire curled region 300 is located in the right ventricle, RV 30 and provides an atraumatic shape that is similar to the shape of the chamber walls and apex 120 of the RV 30. Between the guidewire stiff region 295 and the guidewire curled region 300 is a guidewire transition region 305 that is intermediate both in shape and stiffness between the guidewire transition region 305 and the guidewire curled region 300; the guidewire transition region 305 has more curvature than the guidewire stiff region 295 and less curvature than the guidewire curled region 300; the guidewire transition region 305 is softer than the guidewire stiff region 295 and stiffer than the guidewire curled region 300. As shown in FIG. 8A, the pacing lead 5 has been advanced over the guidewire 290 such that the open distal end 285 of the pacing lead 5 is located across the TCV 25 at a location near the guidewire junction 310 of the guidewire stiff region 295 and guidewire transition region 305.

As shown in FIG. 8B the guidewire 290 is held in a fixed position in space as the pacing lead 5 is advanced over the guidewire 290 into the RV 30, around the apex 120 of the RV 30, and directed proximally upward adjacent the septal wall 130; the guidewire 290, as shown, is extending beyond the open distal end 285 of the pacing lead 5. Further advancement of the pacing lead 5 is shown in FIG. 8C with the guidewire 290 held fixed in position. The pacing lead forms a curled distal region 85 due to its preformed curled shape and can form an overlap portion 105 of a closed loop 95. The guidewire 290 can then be removed from the pacing lead 5 prior to activation of the pacing lead 5 or alternately can remain in place within the lead central lumen 235. Various guidewire 290 shapes and lengths can be used without deviating from the present invention. For example, the guidewire 290 can have a complete coiled loop that overlaps with other portions of the guidewire 290; alternately a smaller length guidewire 290 that extends only a few centimeters into the RV can be used to deliver the pacing lead 5 of the present invention to the RV.

As shown in FIGS. 9A and 9B the open distal end 285 of the pacing lead 5 can provide an end orifice 315 that allows monitoring of blood pressure outside of the curled shaft 80 and within the vasculature of the body or heart 35, or an orifice for delivery of contrast medium or drugs to a region outside of the curled shaft 80 such as the vasculature or heart chambers 508. The open distal end 285 is in direct fluid communication with the manifold port 270 located on the lead manifold 65. The pacing lead 5 can be delivered through the vasculature and into one or more chambers of the heart 35 over a guidewire 290 that extends through the lead body 70 from the lead manifold 65, through the central lumen 235, and out of the open distal end 285 of the pacing lead 5. To deliver contrast medium or obtain a pressure signal from an outside region 268 outside of the curled shaft 80 adjacent to the open distal end 285 of the pacing lead 5, the guidewire 290 can be pulled back such that it is located in the proximal lumen 280 of the pacing lead 5. The distal lumen 265 of the pacing lead 5 should have a distal lumen diameter 275 of preferably 0.020 inches with a range of 0.016-0.030 inches to obtain an undamped pressure signal from the open distal end 285 to the manifold port 270. The hydraulic diameter of the proximal lumen 280 should be similar to the distal lumen diameter 275. Alternately, the guidewire 290 can be removed entirely from the central lumen 235 for delivery of contrast medium, delivery of drugs, or for measurement of pressure within a heart chamber 508 or within the vasculature adjoining the heart 35.

Figure 10A:
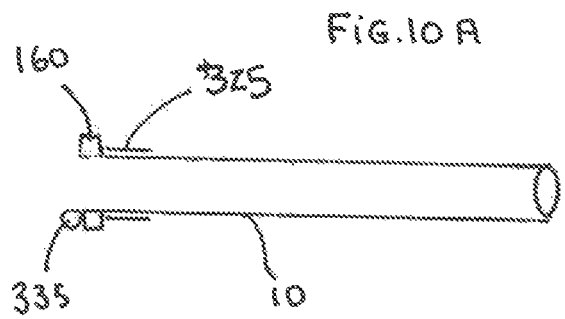
FIG. 10A is a plan view of an introducer sheath having an anode attached near the manifold, the anode is a sleeve anode.
Figure 10B:
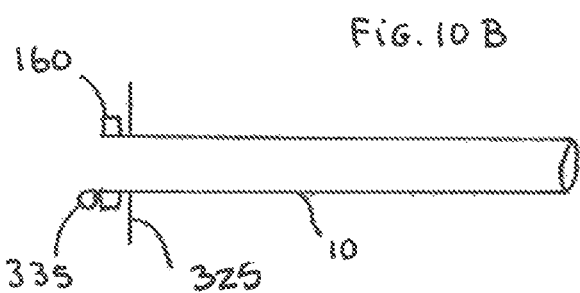
FIG. 10B is a plan view of an introducer sheath having an anode attached near the manifold, the anode is a flange anode.
Figure 10C:
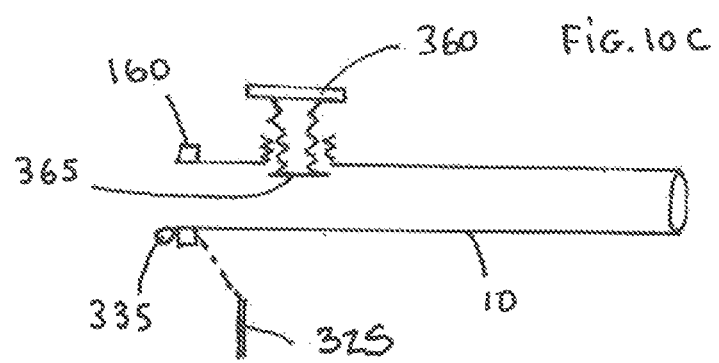
FIG. 10C is a plan view of an introducer sheath having an anode attached near the manifold, the anode is a patch anode; the introducer has a locking screw to provide friction with a pacing lead body to prevent lead migration.

The unipolar temporary pacing lead 5 of the present invention has a cathode 320 comprised of cathode sites 170 located within the pacing lead distal region 85. In further embodiments the anode 325 is located as a component of the introducer sheath 10 as shown in FIGS. 10A-10C. In FIG. 10A the anode 325 is a sleeve anode 330 formed from a metal film that is located around a portion of the introducer sheath 10 that is near the sheath manifold 160 and is in contact with the subcutaneous tissue, the tissue tract, or the vasculature in which the introducer sheath 10 is inserted. The sleeve anode 330 is attached to an anode connector 335 located on the sheath manifold 160. The anode connector 335 is connectable via an anode connecting wire 340 to the positive pole 345 of a pulse generator 220 as shown in FIG. 1A. The sleeve anode 330 can be formed from platinum, silver, or other metal or metal alloys that provide for efficient electrical signal transmission. As shown in FIG. 10B the anode 325 can be a flange anode 350 that is joined or attached to the introducer sheath 10 and forms an electrical continuity with an anode connector 335 located on the sheath manifold 160. The flange anode 350 can be formed from standard metals used to transmit electrical signals; the flange electrode is attached to the subcutaneous tissue via adhesive that is conductive. Another embodiment for the anode 325 is shown in FIG. 10C; a patch anode 355 is electrically coupled to the anode connector 335 located on the sheath manifold 160. The patch anode 355 is attached to the subcutaneous tissue near the access site; the patch electrode is formed from materials similar to those described for the flange electrode. Located on the introducer sheath 10 of the present invention and shown in FIG. 10C is a locking screw 360 that is rotationally activated by the operator to apply a frictional force of a locking plate 365 into direct contact with a pacing lead body 70 that would pass within the introducer sheath. The frictional force between the locking plate 365 and the pacing lead body 70 would prevent inadvertent movement of the pacing lead 5 relative to the introducer sheath 10 thereby reducing the likelihood of loss of capture by a cathode site 170 of the pacing lead 5 with the endocardial surface 140 due to movement of the pacing lead body 70. Other mechanical mechanisms are anticipated to apply a frictional force from the locking plate 365 to the lead body 70 to prevent movement of the pacing lead body 70 relative to the introducer sheath.

In a further alternate embodiment for the present pacing leads having a curled shaft 80, the cathode sites 170 that have been presented in earlier embodiments of the temporary unipolar pacing lead 370 can instead consist of alternating cathode sites 170 and anode sites 380 thereby transforming the unipolar pacing lead 370 of FIG. 2 into a bipolar pacing lead 375 as shown in FIG. 11. Each anode site 380 of the bipolar lead 375 of this embodiment is connected electrically via an anode continuity member 385 to the anode conduction wire 390 that extends via its own electrically insulated path through the lead body 70 to the lead manifold 65 where the anode conduction wire 390 forms an electrical continuity with an anode connector 335. The anode connector 335 is connectable to an anode conduction wire 390 that can be connected to the positive pole 345 (see FIG. 1A) of the pulse generator 220. The cathode site 170 is electrically connected to the cathode conduction wire 180 as described in earlier embodiments. The cathode sites 170 and the cathode conduction wire 180 are each electrically insulated from the anode sites 380 and the anode conduction wire 390. The bipolar pacing lead 375 of this embodiment has a similar curled shaft 80 located in the distal region 85 that is similar to the curled shaft 80 that has been discussed for the unipolar pacing lead 370 shown in FIG. 1A. The anode-cathode site spacing 395 between an anode site 380 and a neighboring cathode site 170 is similar to that provided in current standard pacing leads in order to provide current density to obtain and maintain capture; the anode-cathode site spacing 395 is 1 cm (range 0.5 cm to 2 cm). The paired site distance 405 between the anode-cathode paired sites 400 and a neighboring anode-cathode paired site 400 is 1 cm (range 0.5 cm to 2 cm) and is close enough such that small movements of the pacing lead 5 will allow one anode 325 and one neighboring cathode 320 to become an anode-cathode paired site 400. The coiled shaft 100 plus the multiplicity of anode-cathode paired sites 400 located along the coiled shaft 100 would confer both safety to the pacing lead 5 due to the atraumatic coiled shape of the distal region 85 as well as ease of forming a capture of the myocardium by at least one anode-cathode paired site 400.

It is further understood that each anode site 380 can be connected to a specific anode conduction wire 390 that extends to a specific anode connector 335 located on the lead manifold 65; thus the lead would contain a multiplicity of anode connectors 335 that are electrically insulated from each other and individually connectable to a multiplicity of anode connecting wires 340 to the pulse generator 220. Similarly each cathode site 170 can be connected to a specific cathode conduction wire 180 that extends to a specific cathode connector 185 located on the lead manifold 65; thus the lead would contain a multiplicity of cathode connectors 185 that are electrically insulated from each other and individually connectable to a multiplicity of cathode connecting wires 210 to the pulse generator 220. The pulse generator 220 is able to use an individual anode-cathode paired site 400 to detect a proper location for delivery of a temporary pacing signal. An individual anode-cathode paired site 400 located on the curled shaft 80 could then be activated by the pulse generator 220 in a specific region of the heart chamber 508 that is suitable for temporary pacing in a manner that obviates a potential for diaphragmatic capture, for example.

The previous embodiments of the present invention have shown a curled shaft 80 in a configuration of a coiled shaft 100 that has formed a closed loop 95 with an overlap region and hence the curled shaft 80 of some embodiments can have a coiled shaft 100. Embodiments of the present invention are not required to have a lead closed loop 95 forming an overlap portion 105 extending from the lead distal end 75 to the distal region 85 of a curled shaft 80. Embodiments that do not have a closed loop 95 may instead have an open loop 90 in a lead curled shaft 80 of the lead distal region 85. The lead open loop 90 provides such embodiments with an improved capability to remove the lead curled shaft 80 from the heart chamber 508 following the temporary pacing procedure without snagging and potentially tearing a cordae tendineae 236 of a heart valve 238. The embodiments having the open loop 90 also can be introduced into the chamber of the heart 35 in an atraumatic manner that does not injure the endocardial surface 140 of the heart chamber 508. The embodiments of the temporary pacing lead 5 having an open loop 90 are intended to contain the multiple cathode electrodes 170 or anode electrodes 325 as described in the previous embodiments, the electrodes can be unipolar electrodes or bipolar electrodes as described in earlier embodiments. Additionally, the pacing lead 5 is configured as described in previous embodiments to measure blood pressure via a side orifice 255 or end orifice 315 to detect and identify the chamber of the heart in which the lead distal tip 250 resides. The pacing lead 5 having an open loop 90 can have a closed distal end 240 as shown in some embodiments, or the pacing lead 5 can have an open distal end 285 as described other embodiments such as those shown in FIGS. 8A-8C and 9A-9B.

Lead in a Lead Equilibrium Configuration

Figure 12A:
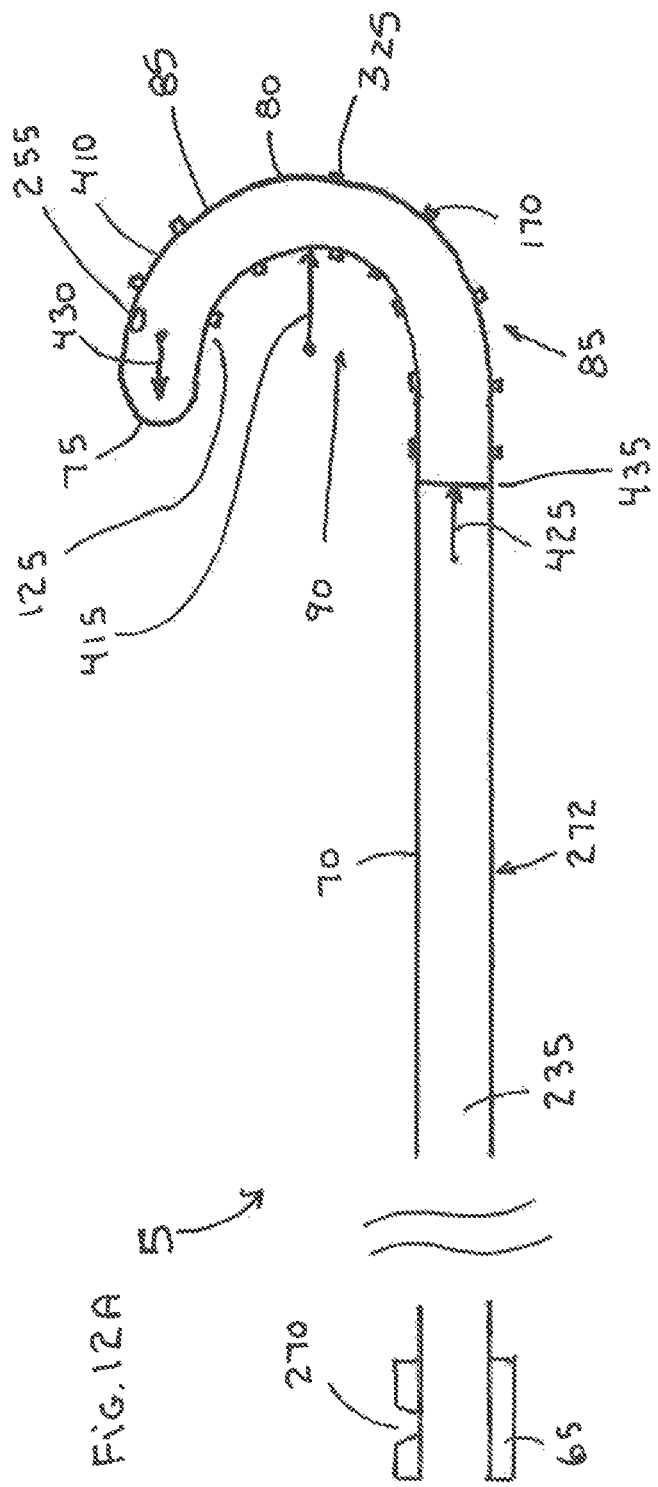
FIG. 12A is a plan view of a temporary pacing lead with a curled shaft showing an open loop.
Figure 12B:
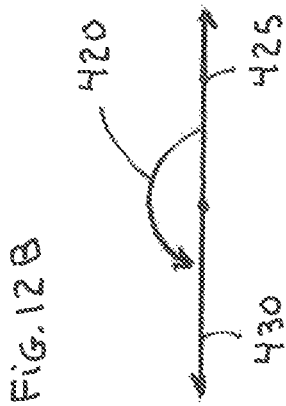
FIG. 12B is a sketch that defines the term lead equilibrium loop angle.
Figure 12F:
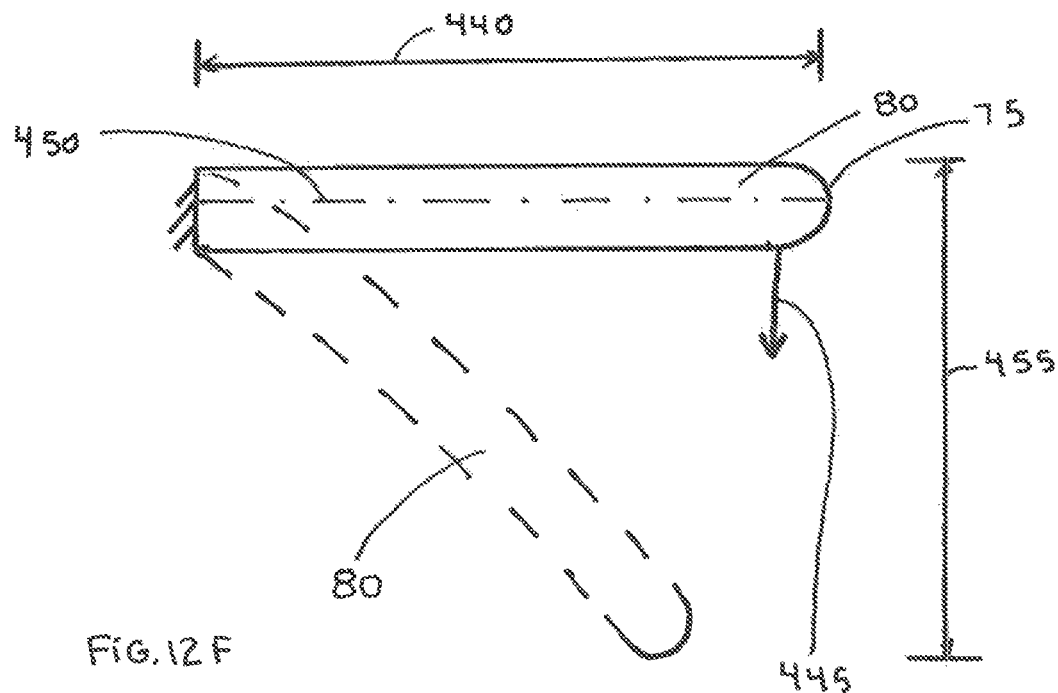
FIG. 12F is a plan view of a distal region of a temporary pacing lead demonstrating the definition of a lead bending modulus.
Figure 12G:
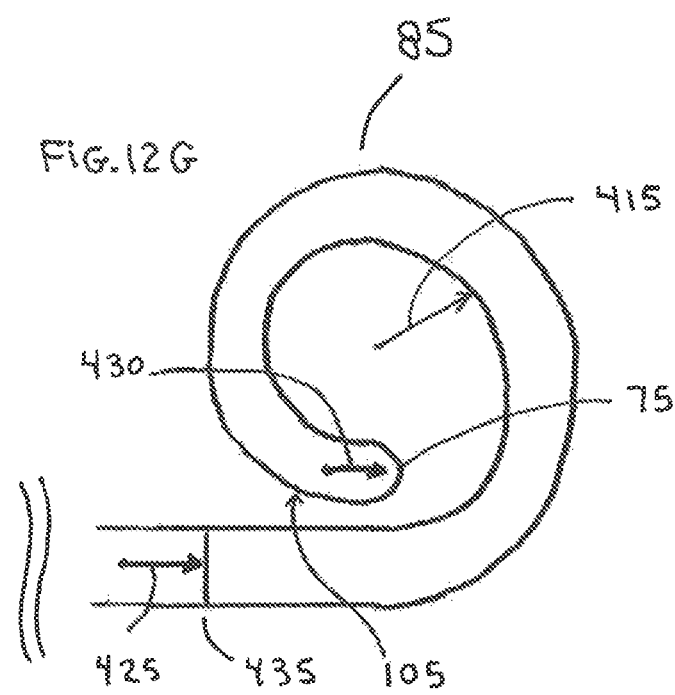
FIG. 12G is a plan view of a distal region of a temporary pacing lead showing a lead equilibrium loop angle of 360 degrees and having an overlap portion.

FIGS. 12A-12F show embodiments for the lead body 70 of the present invention in a lead equilibrium configuration with a lead equilibrium loop 410, i.e., a lead loop without a stylet 230 contained within the lead central lumen 235, and having a lead open loop 90. The lead body 70 has a linearly shaped lead proximal region 272 and a lead curled shaft 80 in the lead distal region 85. The lead curled shaft 80 forms a lead open loop 90 with a lead loop equilibrium radius of curvature 415 of preferably 1 cm and in the range of 0.5-2.0 cm for the lead equilibrium loop 410, i.e., the lead loop equilibrium configuration, such that a stylet 230 is not contained within the lead distal region 85. The lead equilibrium loop angle 420 for the lead equilibrium loop 410, i.e., without a stylet 230, describes the amount of curvature or curl found in the lead curled shaft 80 due to its formed equilibrium shape as shown in FIG. 12B. The lead loop angle 420 for the lead equilibrium loop 410 or other lead loop is the amount of curvature or curl as identified by the lead proximal region direction 425 relative to the lead distal end direction 430. The lead loop angle 420 as shown in FIG. 12A is 180 degrees since the loop distal end direction is 180 degrees opposed from the lead proximal region direction 425 at the lead body junction 435 between the lead proximal region 272 and lead distal region 85. The range for the lead equilibrium loop angle 420 is zero to 360 degrees; a smaller lead equilibrium loop angle 420 provides a greater advantage for removing the lead with an open loop 90 from the heart chamber 508 without entanglement with or tearing of the cordae tendineae 236. The lead loop equilibrium angle of 180 degrees, and ranging from 150-240 degrees, provides an advantageous balance between an atraumatic contact with the endocardial surface 140 during pacing and ease of removing the lead curled shaft 80 from the heart chamber 508 without tearing the cordae tendineae 236. Various lead equilibrium loop angles 420 are anticipated and depicted in FIGS. 12C-12E; FIG. 12C shows a lead distal region 85 with a lead equilibrium loop angle 420 of 270 degrees; FIG. 12D shows a lead equilibrium loop angle 420 of 90 degrees; FIG. 12E shows a lead equilibrium loop angle 420 of zero degrees; variation of the lead equilibrium loop angle 420 are understood to be included in the present invention. It is noted in FIG. 12G that the lead equilibrium loop angle 420 can be 360 degrees as shown in FIG. 12G, where the lead distal tip 250 forms an overlap portion 105 within the lead distal region 85 as described in earlier embodiments of the present invention.

The lead proximal region 272 is stiffer than the lead distal region 85; the lead proximal region 272 is able to provide the necessary push characteristics to allow the lead to be advanced within the vasculature and into the chamber of the heart 35. The lead distal region 85 has a lead bending modulus as defined by FIG. 12F of 0.6 Newtons (range 0.1-5.0 Newtons) and provides the distal region 85 with a soft and floppy characteristic that allows ease of bending. The lead bending modulus preferably ranges from 0.1-1.0 Newtons due to the more advantageous lead removal characteristics for a lead bending modulus that ranges from 0.1-1.0 Newtons. The low lead bending modulus of 0.6 Newtons (range 0.1-1.0 Newtons) allows the lead curled shaft 80 to bend and conform to the surface of the heart chamber 508 without causing tissue ischemia or necrosis at the contact of the curled shaft 80 with the endocardial surface 140. The soft, floppy lead distal region 85 allows the lead to be removed from the heart chamber 508 without entanglement with the cordae tendineae 236 and without tearing the cordae tendineae 236. As shown in FIG. 12F a lead shaft length 440 of the lead curled shaft 80 requires a lead applied force 445 acting perpendicular to the shaft central axis 450 at the lead distal end 75 to generate a lead displacement 455. The ratio of lead displacement 455 per lead shaft length 440 is equal to the lead bending strain of the lead curled shaft 80. The lead bending modulus is equal to: (lead applied force 445)/lead bending strain. Thus for the lead curled shaft 80 the amount of lead applied force 445 to cause a lead curled shaft 80 with a lead bending modulus of 0.6 Newtons to bend to a lead displacement 455 of 1 cm over a 1 cm lead shaft length 440 is 0.6 Newtons. As shown in FIG. 12F, the lead shaft length is shown to be a linear configuration for illustrational purposes. It is understood that similar principles for bending modulus determination apply to a lead curled shaft 80 with a curved or curled shape that is then further bent to an alternate radius of curvature.

Figure 13A:
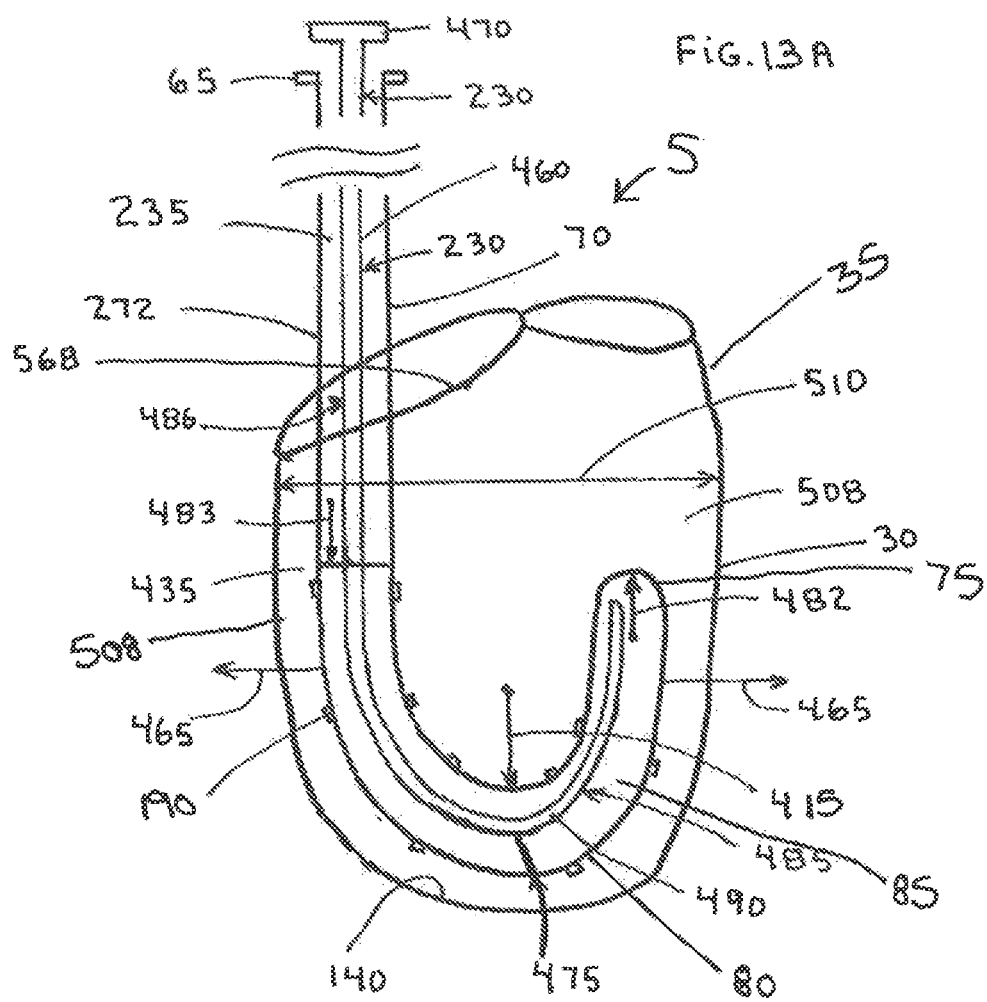
FIG. 13A is a partial perspective view of a temporary pacing lead positioned within a right ventricle and having a stylet contained within the lead central lumen; the lead contacts two walls of the right ventricle.

FIGS. 13A-13G show embodiments of a pacing lead 5 with a lead open loop 90 located within an RV 30 chamber 508 of the heart; a stylet 230 is located in the lead central lumen 235. The stylet 230 is a pacing stylet 460 that can be maintained within the lead central lumen 235 during pacing. FIG. 13A shows a lead distal region 85 located within the right ventricle 30 of the heart 35, for example, and making contact with the endocardial surface 140 of the RV. A straight stylet such as that shown in FIG. 13B can be placed within the lead central lumen 235 (of the lead of FIG. 12A, for example) to cause an outward lead-stylet applied force 465 onto the endocardial surface 140 to provide definite contact of the cathode sites 170 of the cathode electrode 320 with the endocardial surface 140 obtain and maintain capture of the electrical signal.

The stylet 230 has a stylet manifold 470 located at its proximal end to assist in placement depth of the stylet 230 within the lead central lumen 235 and provide rotation of the stylet 230 for rotational alignment of the stylet 230 relative to the lead body 70. The lead-stylet loop 475 has a lead-stylet loop radius of curvature 280 (with the stylet 230 inserted into the lead central lumen 235 and extending to the lead distal end 75) that is 1.5 cm (range 1.0-3.0 cm). The lead-stylet loop angle 481 for the lead-stylet loop 475 as shown in FIGS. 13A and 13C is 180 degrees to provide atraumatic contact with two walls of the endocardial surface 140 and provide an outward lead-stylet applied force 465 in opposite directions against the two opposing walls of the heart chamber 508. The lead-stylet loop angle 481 extends from the lead-stylet distal end direction 482 to the lead-stylet proximal region direction 483 and can range from 150 degrees to more than 360 degrees with the stylet 230 inserted. The lead-stylet loop radius of curvature 280 should be at least 1 cm in order to provide definite contact with the endocardial surfaces 140 on two sides of the heart chamber 508; the lead-stylet loop radius of curvature 280 can be larger, for example, with a lead-stylet loop radius of curvature 280 of up to 3.0 cm.

A straight pacing stylet 460 with a stiffer stylet proximal region that the stylet distal region 485 can provide a larger outward lead-stylet applied force of the lead curled shaft 80 onto the endocardial surface 140 of the heart 35 than a softer stylet distal region 485. The stiffer stylet distal region 485 can be obtained by a larger diameter for the stylet distal region 485 or by altering the temper of a metallic stylet or by altering the material properties of the stylet distal region 485. The outward lead-stylet applied force 465 of the combined lead curved shaft and the stylet curved shaft onto the endocardial surface 140 of the heart 35 is 0.6 Newtons (range 0.1-5 Newtons); preferably, the outward lead-stylet applied force 465 against the endocardium is 0.1-1.0 Newtons; a larger outward force against the endocardial surface 140 providers better contact of the lead distal region 80 with the endocardial surface 140 but can cause unwanted tissue ischemia and necrosis.

Figure 13B:
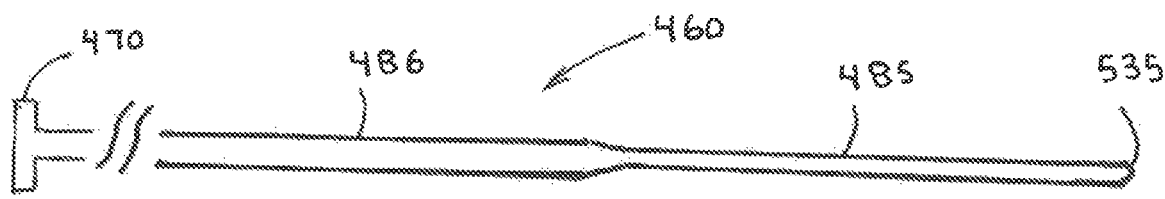
FIG. 13B is a plan view of a straight pacing stylet with a stiffer stylet proximal region and a more flexible stylet distal region.
Figure 13C:
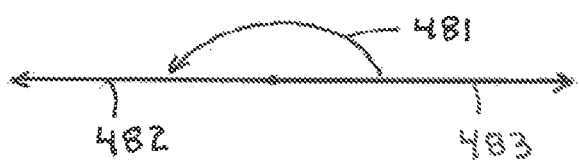
FIG. 13C is a sketch that defines the term lead-stylet loop angle.
Figure 13D:
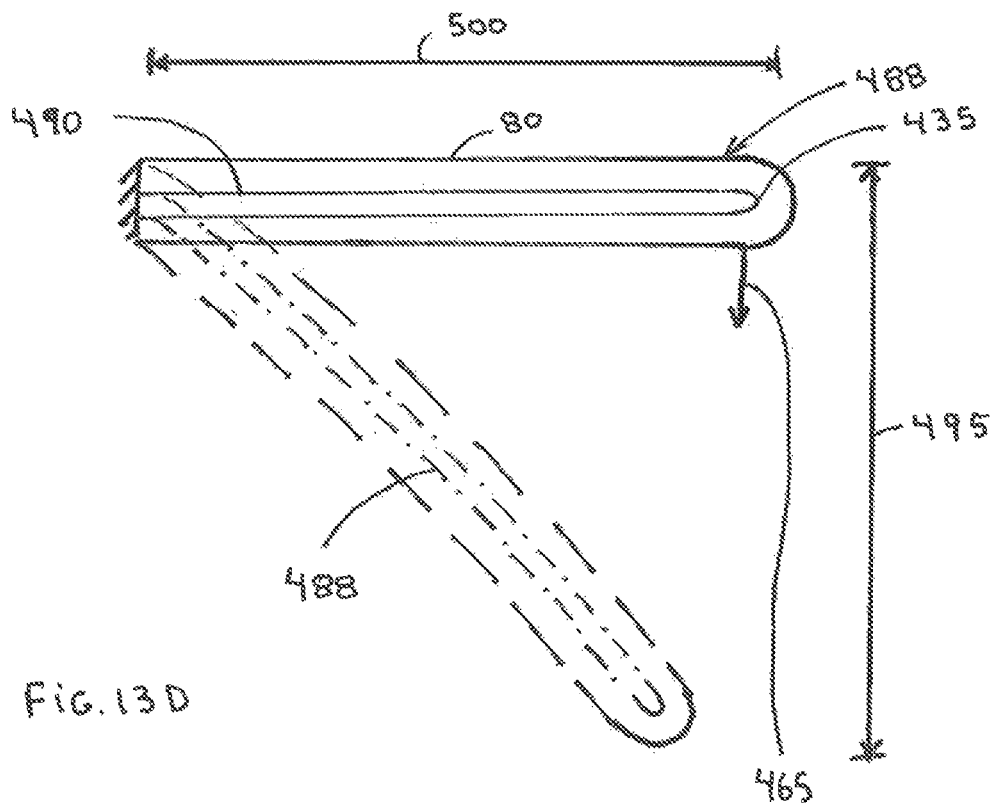
FIG. 13D is a plan view of a distal region of a lead-stylet curled shaft demonstrating the definition of a lead-stylet bending modulus.

The outward lead-stylet applied force 465 provided by the combined material elasticity of the lead curled shaft 80 and the stylet curled shaft 490 (i.e., the lead-stylet curled shaft 488) is determined by the combined lead-stylet bending modulus of the lead curled shaft 80 and the stylet curled shaft 490 as shown in FIG. 13D. The ratio of lead-stylet displacement 495 per lead-stylet shaft length 500 is equal to the lead-stylet bending strain of the lead-stylet curled shaft 488. The lead-stylet bending modulus is equal to: (lead-stylet applied force 465)/lead-stylet bending strain. Thus for the lead-stylet curled shaft 488 the amount of lead-stylet applied force 465 to cause a lead-stylet curled shaft 488 with a lead-stylet bending modulus of 0.6 Newtons to bend to a lead-stylet displacement 495 of 1.5 cm over a 1.5 cm shaft length is 0.6 Newtons. The bending modulus for the stylet distal region 485 is 0.6 Newtons (range 0.1-5.0 Newtons, and preferably 0.1-1.0 Newtons) such that the lead-stylet outward applied force against the endocardium is controlled to 0.6 Newtons (range 0.1-1.0 Newtons). As shown in FIG. 13D, the lead-stylet shaft length 500 is shown to be a linear configuration for illustrational purposes. It is understood that similar principles for bending modulus determination apply to a lead-stylet curled shaft 488 with a curved or curled shape that is then further bent to an alternate radius of curvature.

Figure 13E:
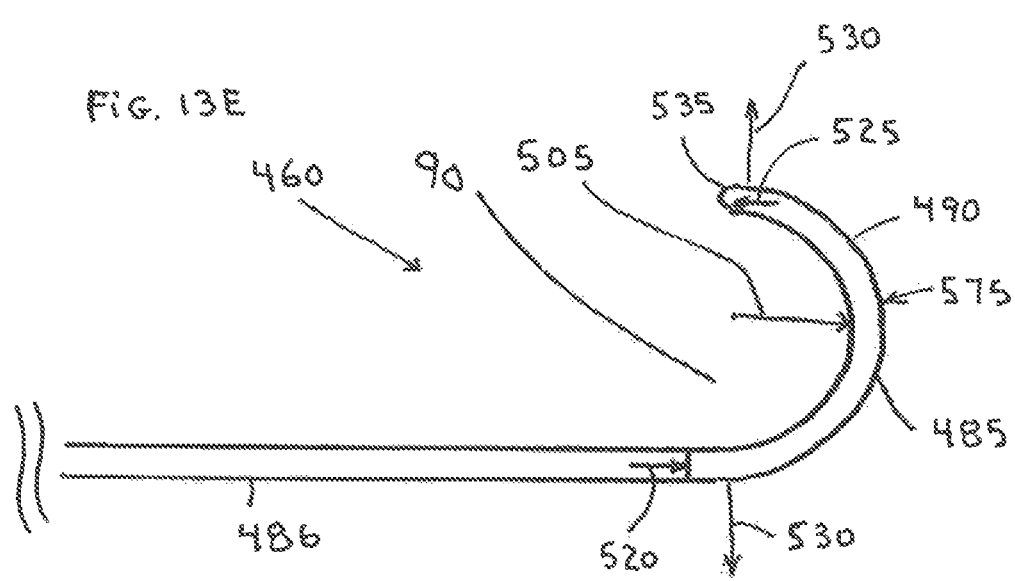
FIG. 13E is a plan view of a distal region of a stylet with a stylet curled shaft showing a stylet radius of curvature.

The pacing stylet 460 can have other configurations other that those shown in FIG. 13B. For example, as shown in FIG. 13E, the pacing stylet 460 can have a stylet radius of curvature 505 of 2.0 cm and can be placed into a lead open loop 90 with a lead loop equilibrium radius of curvature 415 of 1 cm such as shown in FIG. 12A and form a lead-stylet loop 475 with a lead-stylet loop radius of curvature 280 or 1.5 cm, for example, as shown in FIG. 13A. A lead-stylet radius of curvature of preferably 1.5 cm with a range of 1-3 cm will provide suitable contact of the pacing lead 5 with the endocardial surface 140 of the heart chamber 508 and provide electrical signal capture. The stylet radius of curvature 505 can range from 1 cm (for a lead loop equilibrium radius of curvature 415 that is larger than 3 cm, for example) to infinity or a straight stylet, for example, for use in a lead loop equilibrium radius of curvature 415 that is smaller than the heart chamber width 510. The average heart chamber width 510 at a location of contact with the pacing lead body 70 is typical 3 cm with a range of 1-5 cm. The pacing stylet 460 can have a stylet loop angle 515 as described by FIG. 13F that extends from a stylet proximal region direction 520 to a stylet distal end direction 525 of preferably 180 degrees with a range of zero to 360 degrees.

Figure 13F:
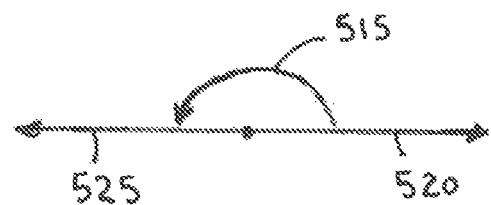
FIG. 13F is a sketch that defines the term stylet loop angle.
Figure 13G:
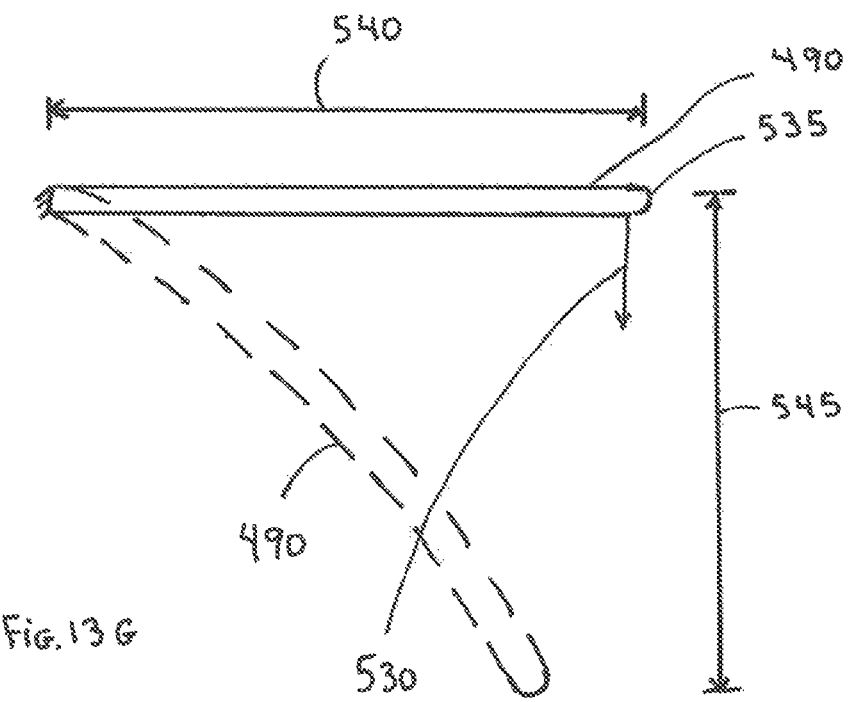
FIG. 13G is a plan view of a distal region of a stylet curled shaft demonstrating the definition of a stylet bending modulus.

The stylet has a stylet bending modulus that is determined by a stylet applied force 530 causing the stylet distal end 535 to bend over a stylet shaft length 540 of the stylet shaft as shown in FIG. 13G. The ratio of stylet displacement 545 per stylet shaft length 540 is equal to the stylet bending strain of the stylet curled shaft 490. The stylet bending modulus is equal to: (stylet applied force 530)/stylet bending strain. Thus for the stylet curled shaft 490 the amount of stylet applied force 530 to cause a stylet curled shaft 490 with a stylet bending modulus of 0.6 Newtons to bend to a stylet displacement 545 of 1 cm over a 1 cm stylet shaft length 540 is 0.6 Newtons. As shown in FIG. 13F, the stylet shaft length is shown to be a linear configuration for illustrational purposes. It is understood that similar principles for bending modulus determination apply to a stylet curled shaft 490 with a curved or curled shape that is then further bent to an alternate radius of curvature.

The stylet of the present invention can have a stylet bending modulus in the stylet distal region 485 that ranges from 0.1-5 Newtons and preferably ranges from 0.1-1.0 Newtons to more closely equal and balance the bending modulus of the lead distal region 85 and provide a suitable outward lead-stylet applied force 465 that does not generate trauma to the endocardial surface 140. The outward lead-stylet applied force 465 will also provide a more linear relationship with respect to lead-stylet displacement 495 if the lead bending modulus and lead loop equilibrium radius of curvature 415 is similar in magnitude to the stylet bending modulus and stylet radius of curvature 505. Thus, the stylet radius of curvature 525, the stylet bending modulus, and the stylet loop angle 515 are combined with the lead loop equilibrium radius of curvature 415, the lead bending modulus, and the lead equilibrium loop angle 420 to determine the lead-stylet loop radius of curvature 480, the lead-stylet loop angle 481, and the outward lead-stylet applied force 465 onto the endocardial surface 140 of the heart 35.

The outward stylet applied force 530 can act in the same outward direction as an outward lead applied force 445, acting against the endocardial surface 140, and hence the two forces are addictive. If the lead curled shaft 80 is of a smaller lead loop radius of curvature than the stylet loop radius of curvature, then the stylet applied force 530 can be acting to enlarge the lead loop radius of curvature and the lead applied force 445 is acting in a direction opposed to the stylet curled shaft 490. The outward forces of the lead applied force 445 and the stylet applied force 530 are expected in the present invention to provide a combined outward lead-stylet applied force 465 onto the endocardial surface 140 of 0.6 Newtons (range 0.1-5.0 Newtons, and preferred range of 0.1-1.0 Newtons) to ensure that tissue ischemia and necrosis of the myocardial tissues 145 are not generated.

For the embodiment wherein the lead curled shaft 80 has a lead loop equilibrium radius of curvature 415 of 1 cm and a stylet has a stylet radius of curvature 505 of 2 cm as described in FIG. 13E, the lead-stylet loop radius of curvature 280 could be 1.5 cm provided that the stylet curled shaft 490 aligned in the same plane and with the same coil direction as the lead curled shaft 80. Such alignment tends to occur naturally as the operator inserts the stylet into the lead central lumen 235. However, if the operator is intending to place the stylet into the lead central lumen 235 such that the lead curled shaft 80 is directly opposed to the stylet curled shaft 490 (i.e., the direction of the stylet loop forms a spiral in a direction that is opposite to the lead loop direction) then an indicator can be located on the stylet manifold 470 and the lead manifold 65 to assist the operator in obtaining the alignment direction that is desired to obtain contact of the lead distal region 80 with the endocardial surface 140 without causing tissue ischemia or necrosis. As shown in FIG. 13H a lead indicator 150 located on the lead manifold 65 can be oriented relative to a stylet indicator 555 located on the stylet manifold 470 to place the orientation of the lead curled shaft 80 in alignment with the stylet curled shaft 490. A locking means such as a screw-type mechanism can be incorporated into the lead indicator 150 and stylet indicator 555 to lock a specific orientation.

Removal of the temporary pacing lead 5 from the chamber of the heart 35 is accomplished by inserting a stylet 230 that can be a removal stylet 560 such as that shown in FIGS. 14A and 14B into the lead central lumen 235 as shown in FIG. 14A. The stylet has a linearly configured stylet proximal region 486 and also a linear stylet central region 487 that extends within a portion of the lead distal region 85. The removal stylet 560 has a curled stylet distal tip 535 that is of a lower bending modulus than the stylet proximal region 486 or stylet central region 487; the stylet distal end 535 can be advanced to a position short of approximation with the lead distal end 75. The stylet serves to straighten a portion of the lead distal region 85 located in the chamber of the heart 35; the stylet distal tip serves as a transition region to allow the lead to be retracted under tension over the stylet 230 until the stylet distal end 535 contacts the lead distal end 75 and further retracted out of the heart chamber 508 along with the stylet 230 such that the lead curled shaft 80 does not entangle with cordae tendineae 236 of the heart chamber 508 as the lead is being retracted under tension.

Introduction of the temporary pacing lead 5 into the vasculature requires that much of the lead body 70 is generally straight except for a curved lead distal tip 250 that can help to negotiate turns within the vasculature and prolapse safely across the TCV. To accomplish the traversal within the vasculature, a generally straight vascular stylet 565 as shown in FIG. 15A can be inserted, for example, into a lead body 70 with an equilibrium configuration as shown in FIG. 15B to provide a combined lead-stylet configuration as shown in FIG. 15C. The lead loop equilibrium radius of curvature 415 can be, for example, 1 cm. The stylet can be stopped proximal to the lead distal tip 75 such that the curled shape of the lead curled shaft provides a small curvature that enables negotiation of vascular turns.

Advancement of the temporary pacing lead 5 into the chamber of the heart 35 requires that the configuration of the curled shaft 80 be rounded and atraumatic to the endocardial surface 140. A proximal secondary bend in the catheter or stylet can give directionality to the lead directing it toward the tricuspid valve annulus and thus entry into the RV. Also, the lead curled shaft 80 must be suitable to traversing the vasculature with a curled shaft 80 suitable to traverse the annulus 568 of the heart 35 and enter the heart chamber 508. The lead loop equilibrium radius of curvature 415 of 1 cm allows the lead curled shaft 80 to form the lead loop within the RA. Withdrawal of the vascular stylet 565 (while maintaining a fixed position for the lead body 70) which can then also serve as a ventricular placement stylet 570 as shown in FIGS. 16A and 16B allows the lead distal region 85 to form a lead equilibrium loop 410 that is suitable (in both a small radius of curvature and a rounded shape) for entering into the heart chamber 508. The lead curled shaft 80 must fit through a 2 cm diameter annulus 568 leading into the ventricular chamber and must have an atraumatic curled configuration that cannot produce trauma to TCV or the endocardial surface 140 of the heart chamber 508. Alternately, to obtain a lead-stylet loop radius of curvature 280 that is smaller than the lead loop equilibrium radius of curvature 415, a shaped ventricular placement stylet 570 having a stylet loop 575 in the stylet curled shaft 490 with a stylet radius of curvature 505 of 0.5 cm, for example, can be introduced into the lead central lumen 235 to cause the lead-stylet loop radius of curvature 480 to be 0.75 cm, for example, as shown in FIGS. 16C and 16D.

The method of use for the temporary pacing lead 5 of the present invention is shown in FIGS. 17-19. In FIG. 17 the lead distal region 85 has been delivered to the RA 20 and the vascular stylet 565 has been withdrawn allowing the lead curled shaft 80 to form an atraumatic shape within the RA as shown in the RA 20 portion of FIG. 17. A ventricular placement stylet 570 may be introduced into the lead central lumen 235, if desired, to form a different lead-stylet curled loop. The pacing lead 5 is then advanced to the apex 120 of the right ventricle, RV 30 also shown in the RV 30 portion of FIG. 17. The lead curled shaft 80 of the lead distal region 85 may obtain a lead loop equilibrium radius of curvature 415 if a stylet is not introduced into the lead distal region 85. If the loop equilibrium radius of curvature is able to provide capture of an electrical signal to the myocardium, then temporary pacing is initiated. If additional outward force or additional outward displacement is needed by the lead curled shaft 80 to make contact with the heart chamber surface, then a pacing stylet 460 is introduced into the lead body central lumen 235 as shown in FIG. 18. The pacing stylet 460 can increase (or decrease; a decrease occurring if the stylet radius of curvature 505 is smaller than the lead loop equilibrium radius of curvature 415) the lead-stylet loop radius of curvature 280 and increase (or decrease; a decrease occurs if the stylet radius of curvature 505 is smaller than the lead-stylet loop radius of curvature 480) the outward force placed onto the endocardial surface 140. Upon completion of temporary pacing, a removal stylet 560 can be placed into the lead central lumen 235 such that a generally linear portion of the stylet extends into the lead distal region 85 to help straighten the lead curled shaft 80 and assist with ease of lead removal. The lead body 70 can be withdrawn proximally under tension while maintaining position of the removal stylet 560 within the lead central lumen 235. The lead curled region distal end 75 is withdrawn toward the stylet distal end 535 such that the lead curled region does not entangle or tear the cordae tendineae 236 as shown in FIG. 19; then, the pacing lead body 70 and stylet 230 can be withdrawn together out of the heart chamber 508. The soft, floppy lead distal region 85 allows the pacing lead 5 to be removed from the heart chamber 508 without entangling the cordae tendineae 236.

The temporary pacing lead 5 having an open loop 90 can have an open distal end 285 as shown in FIG. 20; the lead structure for this embodiment has been described earlier in FIGS. 8A-8C and 9A-9B and also in other embodiments. The stylet that has been described in earlier embodiments to alter the lead loop radius of curvature and alter the outward forces provided by the lead distal region 85 against the myocardial surface can be a guidewire 290. The stylet 230 can be a shaped guidewire 290 that provides atraumatic passage of the lead body 70 over the guidewire 290 through the vasculature, into the heart chamber 508, and during removal of the pacing lead 5 from the chamber of the heart 35. The guidewire 290 can also have a guidewire coiled distal tip 580 or pig-tail, the guidewire coiled tip can be placed adjacent and distal to the lead distal end 75 to provide an atraumatic lead-wire configuration to the lead distal end 75 that allows the lead and guidewire 290 to be advanced together into the chamber of the heart 35 without a need for fluoroscopic guidance.

Control Fiber 585

Figure 21A:
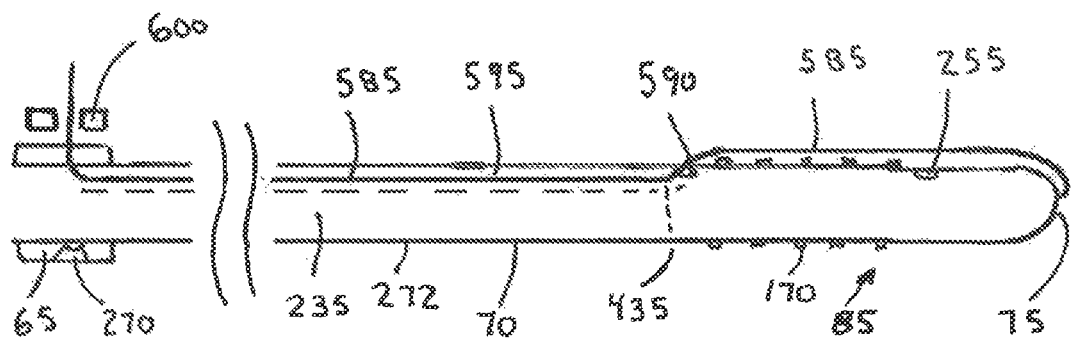
FIG. 21A is a plan view of a temporary pacing lead having a control fiber that can be activated under tension to pull the lead distal end into contact with the lead body to form a closed loop; the lead is in a linear configuration to traverse the vasculature.
Figure 21B:
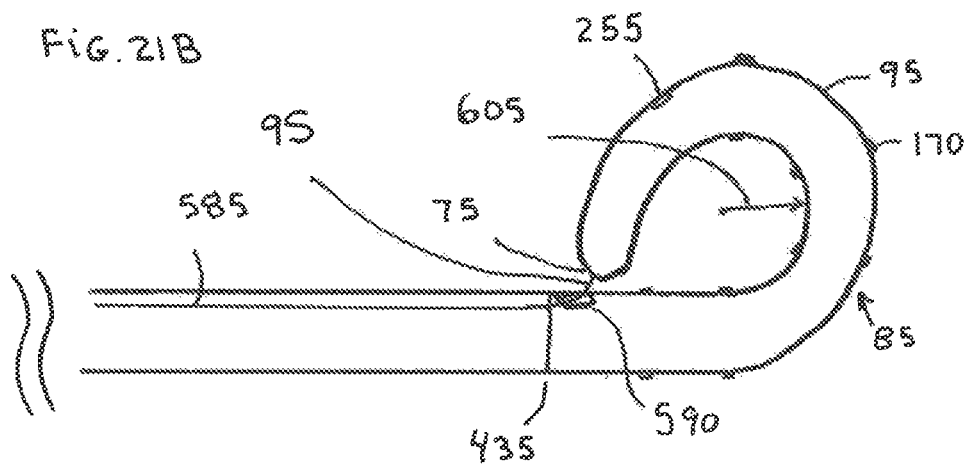
FIG. 21B is a plan view of a temporary pacing lead having a control fiber that can be activated under tension to pull the lead distal end into contact with the lead body to form a closed loop; the lead has formed a closed loop for entry into the heart annulus and for removal from the heart chamber to prevent sub-tricuspid apparatus entanglement.
Figure 21C:
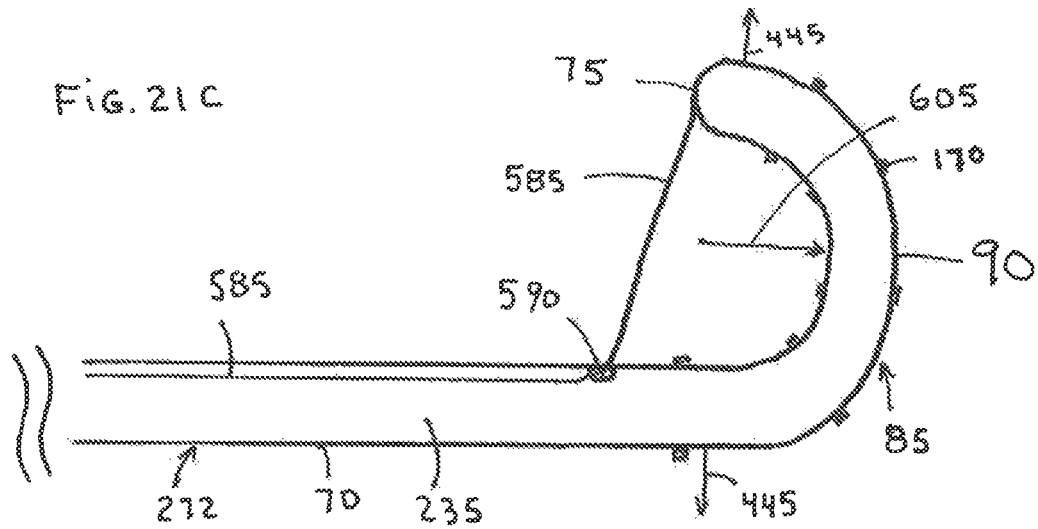
FIG. 21C is a plan view of a temporary pacing lead having a control fiber that can be activated under tension to pull the lead distal end into contact with the lead body to form a closed loop; the lead is in an open loop configuration suitable for pacing the heart chamber.

A further embodiment for the pacing lead 5 of the present invention having multiple electrodes 170, distal pressure measuring capability, and a lead closed loop 95 is shown in FIGS. 21A-21C. FIG. 21A shows the lead distal region 85 of the lead body 70; a control fiber 585 is attached to the lead distal end 75 and traverses external to the lead distal region 85. The control fiber 585 enters a control opening 590 at the lead body junction 435 of the lead proximal region 272 and lead distal region 85. The control fiber 585 extends through a control fiber lumen 595 within the lead proximal region 272 to a lead manifold 65 located at the proximal end of the lead body 70. A holding-tensioning member 600 is attached to the lead manifold 65. The holding-tensioning member 600 is able to take up length of the control fiber 585 and provide tension to the control fiber 585. As shown in FIG. 21A, the lead body 70 is in a linear configuration to traverse the introducer sheath 10. A stylet 230 can be introduced into the lead body central lumen 235 as described in earlier embodiments. The control fiber 585 provides a tension from the lead distal end 75 to the control opening 590 that provides a lead loop controlled radius of curvature 605 to the lead distal region 85 of the lead body 70 as illustrated in FIG. 21B.

Once the lead distal end 75 has traversed through the vasculature and reached the right atrium 20 or the annulus 568 leading to the heart chamber 508, the control fiber 585 can be activated by applying tension via the holding-tensioning member 600. Application of tension causes the lead distal region 85 to form a closed loop 95 as shown in FIG. 21B. The closed loop 95 has a lead loop controlled radius of curvature 605 that allows entry of the closed loop 95 into the chamber of the heart 35 in an atraumatic manner.

Once the lead distal region 85 has been advanced into the chamber of the heart 35, the control fiber 585 can be released to allow the lead distal region 85 to form a curled shaft 80 having loop 90 which remains closed by virtue of the tensioning fiber attachment at the distal lead tip 75 and a fiber controlled opening 590 as shown in FIG. 21C. The outward lead applied force 445 provided by the lead distal region 85 due to the bending energy stored in the lead distal body 70 causes contact between the electrode sites 170 and the endocardial surface 140. The outward lead applied force 445 can be adjusted by introducing a stylet, if necessary, as described in earlier embodiments to provide an outward force of preferably 0.6 Newtons with a range of 0.1-5.0 Newtons. The outward applied force is preferred to have an upper range limit of 1.0 Newtons to ensure that the heart chamber 508 tissue does not become ischemic. Alternatively, the control fiber 585 can be released an additional amount or can be retracted under tension to alter the outward lead applied force 445 inherent in the stored bending energy of the lead distal region 85 onto the endocardial surface 140.

Removal of the pacing lead 5 is accomplished by applying tension to the control fiber 585 via the holding-tensioning member 600 to place the lead distal region 85 into a closed loop 95 as shown in FIG. 21B. The pacing lead 5 can be pulled back under tension into the RA 20 where the control fiber 585 can be released to allow the lead distal region 85 to form a linear configuration as shown in FIG. 21A. Alternately, the control fiber 585 can be released of all tension within the heart chamber 508 allowing the lead body 70 to assume a more linear shape similar to that of FIG. 21A prior to removing the lead body 70 from the heart chamber 508. Since the lead distal tip 250 is attached to the lead body 70 via the control fiber 585 at the control fiber opening 590, entanglement of the lead distal region 85 with cordae tendineae 236 is obviated.

Any version of any component or method step of the invention may be used with any other component or method step of the invention. The elements described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference in their entirety to the same extent as if each individual reference were specifically and individually indicated as being incorporated by reference. In case of conflict between the present disclosure and the incorporated references, the present disclosure controls.

The devices, methods, compounds and compositions of the present invention can comprise, consist of, or consist essentially of the essential elements and limitations described herein, as well as any additional or optional steps, ingredients, components, or limitations described herein or otherwise useful in the art.

While this invention may be embodied in many forms, what is described in detail herein is a specific preferred embodiment of the invention. The present disclosure is an exemplification of the principles of the invention is not intended to limit the invention to the particular embodiments illustrated. It is to be understood that this invention is not limited to the particular examples, process steps, and materials disclosed herein as such process steps and materials may vary somewhat. It is also understood that the terminology used herein is used for the purpose of describing particular embodiments only and is not intended to be limiting since the scope of the present invention will be limited to only the appended claims and equivalents thereof.

The invention claimed is:

1. A pacing lead for temporary atraumatic placement via transvascular access on an endocardial surface of a heart chamber of an animal body part to deliver an electrical signal comprising:
   a. a lead manifold located outside the animal body; and
   b. a pacing lead body connected to the lead manifold, the pacing lead body having a proximal end and a distal end, wherein the pacing lead body comprises a curled shaft having a distal end and a proximal end and a flexible shaped curved memory, wherein the curled shaft is located in the distal end of the pacing lead body for placement of the lead body against the surface of the body part, the curled shaft further including a plurality of cathode sites, which cathode sites are connected via electrical continuity such that at least one of the plurality of the cathode sites is adapted to be temporarily connected to the wall surface, wherein each of the plurality of cathode sites is connected to a specific cathode conduction wire for the cathode site and selected from a plurality of cathode conduction sires, wherein each of the plurality of cathode conduction wires extends along the pacing lead body to connect to an individual connector which is specific for the selected conduction wire on the lead manifold, wherein each of the plurality of cathode connectors is dimensioned and configured to be connected via a cathode connecting wire to a negative pole of a pulse generator, and wherein the pulse generator provides voltage and current to at least one of the plurality of cathode sites.

2. The pacing lead of claim 1, wherein the pacing lead is a unipolar lead.

3. The pacing lead of claim 1, wherein the pacing lead is a bipolar lead comprising a plurality of alternating cathode sites and anode sites on the pacing lead body, wherein each of the plurality of anode sites is connected to an individual anode conduction wire, wherein each of the individual anode conduction wires is electrically insulated from another anode conduction wire, and wherein each of the individual anode conduction wires is connected to an individual anode connector located on the lead manifold wherein the pulse generator provides voltage and current to the individual anode connector.

4. The pacing lead of claim 1, wherein the curled shaft forms a loop angle ranging from 150 to 240 degrees and comprises an outward memory force, thereby being configured to contact opposing wall surfaces of the chamber.

5. The pacing lead of claim 1, wherein the curled shaft has a curled shaft radius of curvature between about 0.05 and 3.0 cm.

6. The pacing lead of claim 1, wherein the curled shaft comprises an open loop such that the lead body distal end does not overlap with the curled shaft proximal end.

7. The pacing lead of claim 1, wherein the curled shaft comprises a closed loop such that the distal end of the pacing lead overlaps with the proximal end of the curled shaft.

8. The pacing lead of claim 1, wherein the pacing lead body has an echogenic coating applied thereto wherein the echogenic coating aids in visualizing the pacing lead under echo guidance during initial placement or repositioning of the pacing lead.

9. The pacing lead of claim 1, further comprising an introducer sheath to assist in the placement of the pacing lead within the chamber, wherein the introducer sheath comprises an inner surface and an outer surface, wherein the pacing lead is adapted to extend distally through the introducer sheath.

10. The pacing lead of claim 9, wherein the introducer sheath includes an anode site positioned of the outer surface of the introducer sheath.

11. The pacing lead of claim 10, wherein the anode site is electrically coupled to a temporary pulse generator.

12. The pacing lead of claim 1, wherein the distal end of the lead body comprises at least one orifice, wherein the at least one orifice is in direct fluid communication with the internal lumen of the lead body.

13. The pacing lead of claim 1, wherein the lead body has an open distal end.

14. The pacing lead of claim 1, further comprising a control fiber connected to the lead body distal end, wherein the control fiber traverses external to the lead body distal region, wherein the lead body includes a control fiber opening at the proximal of the curled shaft, wherein the control fiber extends through the control opening into a control fiber lumen within the lead body to the lead manifold at the proximal end of the lead body, wherein the lead manifold includes a holding-tensioning member for securing the control fiber and providing tension to the control fiber.

15. A pacing lead for temporary atraumatic placement via transvascular access on an endocardial surface of a heart chamber of an animal body to deliver an electrical signal comprising:
   a. a lead manifold located outside the animal body; and
   b. a pacing lead body connected to the lead manifold, the pacing lead body having a proximal end and a distal end, wherein the pacing lead body comprises a curled shaft having a distal end and a proximal end and a flexible shaped curved memory, wherein the curled shaft is located in the distal end of the pacing lead body for placement of the lead body against the surface of the body part, the curled shaft further including a plurality of cathode sites, which cathode sites are connected via electrical continuity such that at least one of the plurality of the cathode sites is adapted to be temporarily connected to the wall surface, wherein each of the plurality of cathode sites is connected one of a plurality of cathode conduction wires, wherein each of the plurality of cathode conduction wires extends along the pacing lead body to connect to one of a plurality of cathode connectors on the lead manifold, wherein each of the plurality of cathode connectors is dimensioned and configured to be connected via a cathode connecting wire to a negative pole of a pulse generator, wherein the pulse generator provides voltage and current to at least one of the plurality of cathode sites, where each of the plurality of cathode sites is formed by a ring electrode encircling the curled shaft; and
   c. an internal lumen having a proximal end and a distal end for receiving a placement stylet.

16. The pacing lead of claim 15, wherein the placement stylet is linear shaped.

17. The pacing lead of claim 15, wherein the placement stylet is curved.

18. The pacing lead of claim 15, wherein the distal end of the internal lumen is closed such that the stylet is dimensioned and configured to extend within the internal lumen of the pacing lead but cannot extend distally beyond the closed distal end.

19. The pacing lead of claim 15, wherein the distal end of the internal lumen is open such that the stylet is dimensioned and configured to extend within the internal lumen of the pacing lead and through the open distal end.

20. A method of temporarily and transvascularly placing a pacing lead on an endocardial surface of a heart chamber of an animal body, wherein the pacing lead comprises a lead manifold located outside the animal body; and a pacing lead body connected to the lead manifold, the pacing lead body having a proximal end and a distal end, wherein the pacing lead body comprises a curled shaft having a distal end and a proximal end and a flexible shaped curved memory, wherein the curled shaft is located in the distal end of the pacing lead body for placement of the lead body against the surface of the body part, the curled shaft further including a plurality of cathode sites, which cathode sites are connected via electrical continuity such that at least one of the plurality of the cathode sites is adapted to be temporarily connected to the wall surface, wherein each of the plurality of cathode sites is connected one of a plurality of cathode conduction wires, wherein each of the plurality of cathode conduction wire extends along the pacing lead body to connect to one of a plurality of cathode connectors on the lead manifold, wherein each of the plurality of cathode connectors is dimensioned and configured to be connected via a cathode connecting wire to a negative pole of a pulse generator, wherein the pulse generator provides voltage and current to the plurality of cathode sites, where each of the plurality of cathode sites is formed by a ring electrode encircling the curled shaft; and an internal lumen having a proximal end and a distal end for receiving a placement stylet, the method comprising:
   a. slidingly advancing the placement stylet within the internal lumen toward the distal end of the lead body of the pacing lead to cause the lead distal region to form a generally linear shape;
   b. advancing the pacing lead through the introducer sheath toward the heart chamber;

c. holding the stylet in a fixed position and advancing the pacing lead distally into the heart chamber;
d. slidingly removing the stylet from the distal end of the lead body of the pacing lead, such that the distal end initiates the formation of the curled shaft within the heart chamber; and
e. advancing the temporary pacing lead further while maintaining the stylet at a fixed position to allow the lead distal end to form an equilibrium configuration of a curved loop.

* * * * *